US 7,553,338 B2
Jun. 30, 2009

(12) United States Patent
Weser et al.

(10) Patent No.: US 7,553,338 B2
(45) Date of Patent: Jun. 30, 2009

(54) **COLOR-MODIFYING COMPOSITIONS CONTAINING A *MORINGA* PLANT SEED PROTEIN AND METHODS OF TREATING KERATIN FIBERS THEREWITH**

(75) Inventors: Gabriele Weser, Neuss (DE); Elisabeth Poppe, Hamburg (DE); Astrid Kleen, Hamburg (DE); Wolfgang Wolff, Bargteheide (DE); Mustafa Akram, Hamburg (DE)

(73) Assignee: Henkel KGaA, Dusseldorf (DE)

( * ) Notice: Subject to any disclaimer, the term of this patent is extended or adjusted under 35 U.S.C. 154(b) by 0 days.

(21) Appl. No.: 11/663,043

(22) PCT Filed: Sep. 8, 2005

(86) PCT No.: PCT/EP2005/009666

§ 371 (c)(1),
(2), (4) Date: Mar. 16, 2007

(87) PCT Pub. No.: WO2006/032374

PCT Pub. Date: Mar. 30, 2006

(65) Prior Publication Data

US 2008/0104773 A1 May 8, 2008

(30) Foreign Application Priority Data

Sep. 16, 2004 (DE) ............... 10 2004 045 322
Dec. 21, 2004 (DE) ............... 10 2004 062 702

(51) Int. Cl.
*A61Q 5/10* (2006.01)
(52) U.S. Cl. ............... 8/405; 8/406; 8/426; 8/435; 8/646
(58) Field of Classification Search ............... 8/405, 8/406, 426, 435, 646
See application file for complete search history.

(56) References Cited

U.S. PATENT DOCUMENTS

| 3,753,968 | A | 8/1973 | Ward |
| 4,324,780 | A | 4/1982 | Jacquet et al. |
| 4,814,101 | A | 3/1989 | Schieferstein et al. |
| 4,865,774 | A | 9/1989 | Fabry et al. |
| 4,931,218 | A | 6/1990 | Schenker et al. |
| 4,994,088 | A | 2/1991 | Ando et al. |
| 5,061,289 | A | 10/1991 | Clausen et al. |
| 5,136,093 | A | 8/1992 | Smith |
| 5,294,726 | A | 3/1994 | Behler et al. |
| 5,380,340 | A | 1/1995 | Neunhoeffer et al. |
| 5,494,489 | A | 2/1996 | Akram et al. |
| 5,534,267 | A | 7/1996 | Neunhoeffer et al. |
| 5,663,366 | A | 9/1997 | Neunhoeffer et al. |
| 5,766,576 | A | 6/1998 | Löwe et al. |
| 6,284,003 | B1 | 9/2001 | Rose et al. |
| 6,338,741 | B1 | 1/2002 | Vidal et al. |
| 6,500,470 | B1 * | 12/2002 | Pauly ............... 424/776 |
| 6,528,075 | B1 | 3/2003 | Brown et al. |
| 6,645,258 | B2 | 11/2003 | Vidal et al. |
| 6,667,047 | B2 | 12/2003 | Brown et al. |
| 6,719,811 | B1 | 4/2004 | Konrad et al. |
| 2001/0021388 | A1 | 9/2001 | Motitschke et al. |
| 2002/0088063 | A1 * | 7/2002 | Ohashi et al. ............... 8/405 |
| 2003/0198629 | A1 | 10/2003 | Brown et al. |

FOREIGN PATENT DOCUMENTS

| CA | 2366826 | 10/2000 |
| DE | 23 59 399 | 6/1975 |
| DE | 28 17 369 | 10/1978 |
| DE | 37 23 354 | 1/1989 |
| DE | 37 25 030 | 2/1989 |
| DE | 38 43 892 | 6/1990 |
| DE | 39 26 344 | 2/1991 |
| DE | 39 29 973 | 3/1991 |
| DE | 41 33 957 | 4/1993 |
| DE | 4408 506 | 9/1995 |
| DE | 195 43 988 | 5/1997 |
| DE | 195 44 655 | 6/1997 |
| DE | 197 56 454 | 6/1999 |
| DE | 199 14 926 | 2/2000 |
| DE | 199 14 927 | 10/2000 |
| DE | 100 61 419 | 6/2002 |
| EP | 217 274 | 4/1987 |
| EP | 283 817 | 9/1988 |
| EP | 530 229 | 6/1995 |
| EP | 0 671 161 | 9/1995 |
| EP | 740 931 | 11/1996 |
| FR | 2 776 519 | 10/1999 |
| GB | 1026978 | 4/1966 |
| GB | 1153196 | 5/1969 |
| GB | 1 486 576 | 9/1977 |
| GB | 2 104 091 | 3/1983 |
| JP | 02019576 | 1/1990 |
| WO | WO-91/03229 | 3/1991 |
| WO | WO-92/13829 | 8/1992 |
| WO | WO-94/08969 | 4/1994 |
| WO | WO-94/08970 | 4/1994 |
| WO | WO-96/15765 | 5/1996 |
| WO | WO-99/32216 | 7/1999 |
| WO | WO-2004/112745 | 12/2004 |

OTHER PUBLICATIONS

Laboratories Serobiologiques, Online, "Puricare TM—The new "2 in 1" anti-stress, anti-pollution for hair", Nov. 15, 2005, pp. 1-2.

(Continued)

*Primary Examiner*—Eisa B Elhilo
(74) *Attorney, Agent, or Firm*—Connolly Bove Lodge & Hutz LLP

(57) ABSTRACT

Compositions suitable for treating keratin fibers, which compositions comprise: (a) a protein from a seed of a plant of the *Moringa* genus; (b) a color-modifying active ingredient; and (c) a cosmetically-acceptable carrier component are disclosed along with methods of using and making the same.

20 Claims, No Drawings

OTHER PUBLICATIONS

Armand-Stussi et al,. "An Interesting Source of Moringa oleifera—Active Ingredients for Skin and Hair Care," *Personal Care*, May 2003, pp. 7-14.

Zviak, "Hair Coloring, Nonoxidation Coloring," *The Science of Hair Care*, Chapter 7, pp. 235-261, Marcel Dekker, Inc., New York and Basel.

Zviak, "Oxidation Coloring," *The Science of Hair Care*, Chapter 8, pp. 263-286, Marcel Dekker, Inc., New York and Basel.

Industrieverband Körperpflege-u. Waschmittel e. V,"Leitfaden zur Inhaltsstoffdeklaration kosmetischer Mittel", 1995.

Schrader, *Grundlagen und Rezepturen der Kosmetika* [Fundamentals and formulations of cosmetics], 2nd edition, Hüthig Buch Verlag, Heidelberg, 1989.

"Inorganic Pigments, Maufacturing Process, 'Mica Flake-Based Pigments Suitable for Cosmetic Use,'" *Chemical Technology Review*, No. 166, 1980, pp. 161-173.

"Luster Pigments," *Industrial Inorganic Pigments*, 2nd edition, Wiley-VCH, Weinheim, 1998, pp. 211-231.

"*International Cosmetic Ingredient Dictionary and Handbook*", (seventh edition 1997, vols. 1 and 2, The Cosmetic, Toiletry, and Fragrance Association, 1101 17th Street, N.W., Suite 300, Washington, DC 20036-4702).

* cited by examiner

COLOR-MODIFYING COMPOSITIONS CONTAINING A *MORINGA* PLANT SEED PROTEIN AND METHODS OF TREATING KERATIN FIBERS THEREWITH

CROSS-REFERENCE TO RELATED APPLICATIONS

This application is a national stage application, under 35 U.S.C. §371, of PCT/EP2005/009666, filed Sep. 8, 2005, which claims priority of German Application No. 10 2004 045 322.5, filed Sep. 16, 2004, and German Application No. 10 2004 062 702.9,filed Dec. 21, 2004.

BACKGROUND OF THE INVENTION

1. "Color-Modifying Agents Comprising Moringa Extract"

The present application relates to color-modifying agents for keratin fibers comprising, besides direct dyes and/or dye precursors, at least one protein of the seed of the genus of the *moringa* plants.

Human hair is nowadays treated in diverse ways with hair cosmetic preparations. These include, for example, cleansing the hair using shampoos, care and regeneration using rinses and treatments, as well as bleaching, coloring and shaping the hair using colorants, tints, waving compositions and styling preparations. In this regard, compositions for changing or nuancing the color of head hair play a prominent role.

For temporary colorations, use is usually made of colorants or tints which comprise so-called direct dyes as coloring component. These are dye molecules which attach directly to the hair and require no oxidative process to develop the color. These dyes include, for example, henna, which has been known since antiquity for coloring body and hair. These colorations are usually significantly more sensitive toward shampooing than the oxidative colorations, meaning that an often undesired nuance shift or even a visible "decoloration" arises very much more quickly.

For lasting, intense colorations with corresponding fastness properties, use is made of so-called oxidation colorants. Such colorants usually comprise oxidation dye precursors, so-called developer components and coupler components. Under the influence of oxidizing agents or of atmospheric oxygen, the developer components form the actual dyes with one another or with coupling with one or more coupler components. The oxidation colorants are characterized by excellent, long-lasting coloring results. For natural-looking colorations, a mixture of a relatively large number of oxidation dye precursors usually has to be used; in many cases, in addition, direct dyes are used for the nuancing.

Finally, in recent times, a new type of dyeing method has received much attention. In this method, precursors of the natural hair dye melanin are applied to the hair; in the course of oxidative processes within the hair, these then form nature-analogous dyes. One such method using 5,6-dihydroxyindoline as dye precursor has been described in EP-B1-530 229. Upon application, in particular repeated application, of compositions containing 5,6-dihydroxyindoline it is possible to restore the natural hair color in people with gray hair. The coloring can take place here with atmospheric oxygen as a single oxidizing agent, meaning that recourse does not have to be made to further oxidizing agents. For people with originally medium-blonde to brown hair, indoline can be used as the sole dye precursor. For use in the case of people with an originally red and in particular dark to black hair color, by contrast, satisfactory results can often only be achieved through co-use of further dye components, in particular specific oxidation dye precursors.

In order to improve the care state of the fibers, it has been customary for some time to subject the fibers to a special aftertreatment following the color-changing treatment. Here, the hair is treated, usually in the form of a rinse, with special active ingredients, for example quaternary ammonium salts or special polymers. Depending on the formulation, this treatment improves combability, hold and fullness of the hair and reduces the number of split ends.

In recent times, so-called combination preparations have also been developed in order to reduce the expenditure of the customary multistage methods, particularly in the case of direct application by consumers.

Besides the customary components, for example for coloring the hair, these preparations additionally comprise active ingredients which were previously reserved for hair aftertreatment compositions. The consumer thus saves one application step; at the same time, the packaging expenditure is reduced since one less product is used.

The active ingredients which can be used for the purposes of such combination preparations have to satisfy high requirements, especially with regard to their stability, since the coloring creams usually have a high pH and the oxidizing agent preparations have a low pH. Incompatibilities of the various active ingredients with one another and thus low storage stability are also to be avoided.

Within the scope of the applications DE-A-199 14 927, DE-A-199 14 926 and DE-A44 08 506, such active ingredient combinations have already been proposed for use in oxidative colorants. However, these compositions also leave something to be desired with regard to the care properties, particularly on fibers which are difficult to care for, such as, for example, Japanese hair.

There is therefore still a need for care active ingredients for the color-modifying treatment of fibers. In addition, it was the object of the present invention to develop a color-modifying agent which simultaneously protects the fibers against the harmful effect of UV radiation.

BRIEF SUMMARY OF THE INVENTION

Surprisingly, it has now been found that color-modifying agents which, besides the color-imparting components, comprise at least one protein of the seed of the genus of the *moringa* plants are stable and also develop an excellent care effect.

The present application therefore firstly provides an agent for coloring keratin fibers which comprises, in a cosmetically acceptable carrier, (A) at least one protein of the seed of the genus of the *moringa* plants and (B) at least one color-modifying active ingredient.

According to the invention, "keratin fibers" are to be understood here as meaning furs, wool, feathers and in particular human hair.

According to the invention, besides the proteins in their natural form, the term "protein of the seed of the genus of the *moringa* plants" also includes the derivatives of these proteins that can be produced by chemical and/or enzymatic conversion, such as, for example, the protein hydrolyzates and the quaternized derivatives of the seed of this plant genus.

DETAILED DESCRIPTION OF THE INVENTION

It has already been known for a long time to use proteins or modified proteins in cosmetic preparations to achieve care effects. For this purpose, either water-soluble proteins or proteins modified by chemical and/or by enzymatic reactions, i.e. rendered water-soluble, are used. Even during the reactions for achieving adequate solubility in water, such extensive degradation is often required in the case of fiber proteins that the cosmetic effectiveness is no longer adequate. In recent times, plant proteins and their hydrolyzates and derivatives are used more and more often in cosmetics. For example, products based on wheat, oats, rice, corn, potatoes or soya are known.

The plants which comprise interesting effective ingredients include the family of *moringa* plants. *Moringa* plants have been known since antiquity. Plants of this type are better known under their trivial name "wonder tree". They are preferably indigenous in tropical areas. The different parts of this plant genus have been used since antiquity, especially for medicinal purposes.

The genus of the *moringa* plants includes about 14 species. One of these is *Moringa oleifera* (*Moringa pterygosperma*). Further species are, for example, *Moringa drouhardii*, *Moringa concanensis* or *Moringa peregrina*. The protein is obtained from the seeds of the *moringa* plants by gentle extraction with water and glycerol. This protein has a molecular weight of from 500 to 50 000 daltons. Preference is given to a protein extract with a molecular weight of from 3000 to 30 000 daltons, very particularly preferably from 5000 to 15 000 daltons. According to the invention, particular preference is given to an extract which is obtained from the plant *Moringa oleifera*. In addition, the extract according to the invention can of course comprise water and glycerol on account of the extraction. The content of extracted protein in the extract is 0.01 to 20% by weight. A content of protein of from 0.01 to 10% by weight is preferred here. Particular preference is given to an extract with a protein content of from 0.01 to 5% by weight. Furthermore, at least 30% by weight of glycerol is present in the extract. Finally, water is present in the extract according to the invention. Such a protein is commercially available, for example, under the trade name Puricare® LS 9658 from Laboratoires Sérobiologiques.

The above-described protein extract from the seeds of the *moringa* plants is present in the cosmetic compositions in an amount of from at least 0.01 to 20% by weight. Preference is given to using extract amounts of from 0.01 to 10% by weight, very particularly preferably amounts of from 0.01 to 5% by weight, based on the total cosmetic composition.

Within the scope of a first preferred embodiment, the color-modifying active ingredient is a dye precursor and/or a direct dye.

With regard to the dye precursors which can be used in the colorants according to the invention, the present invention is not subject to limitations of any kind. The colorants according to the invention can comprise, as dye precursors, oxidation dye precursors of the developer type and/or coupler type, and precursors of nature-analogous dyes, such as indole and indoline derivatives, and mixtures of representatives of these groups.

Within the scope of a first preferred embodiment of the present invention, the compositions according to the invention comprise at least one dye precursor of the developer type and/or coupler type.

According to the invention, it may be preferred to use a p-phenylenediamine derivative or one of its physiologically compatible salts as developer component. Particular preference is given to p-phenylenediamine derivatives of the formula (E1)

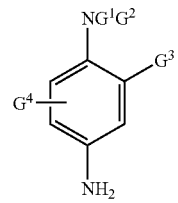

(E1)

where

G$^1$ is a hydrogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)alkoxy(C$_1$- to C$_4$)alkyl radical, a 4'-aminophenyl radical or a C$_1$- to C$_4$-alkyl radical which is substituted by a nitrogen-containing group, a phenyl radical or a 4'-aminophenyl radical, G$^2$ is a hydrogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)alkoxy(C$_1$- to C$_4$)alkyl radical or a C$_1$- to C$_4$-alkyl radical which is substituted by a nitrogen-containing group, G$^3$ is a hydrogen atom, a halogen atom, such as a chlorine, bromine, iodine or fluorine atom, a C$_1$- to C$_4$-alkyl radical, a C$_1$- to C$_4$-monohydroxyalkyl radical, a C$_2$- to C$_4$-polyhydroxyalkyl radical, a C$_1$- to C$_4$-hydroxyalkoxy radical, a C$_1$- to C$_4$-acetylaminoalkoxy radical, a C$_1$- to C$_4$-mesylaminoalkoxy radical or a C$_1$- to C$_4$-carbamoylaminoalkoxy radical, G$^4$ is a hydrogen atom, a halogen atom or a C$_1$- to C$_4$-alkyl radical or if G$^3$ and G$^4$ are in the ortho position relative to one another, they can together form a bridging α,ω-alkylenedioxo group, such as, for example, an ethylenedioxy group.

Examples of the C$_1$- to C$_4$-alkyl radicals specified as substituents in the compounds according to the invention are the groups methyl, ethyl, propyl, isopropyl and butyl. Ethyl and methyl are preferred alkyl radicals. C$_1$- to C$_4$-alkoxy radicals preferred according to the invention are, for example, a methoxy or an ethoxy group. In addition, preferred examples of a C$_1$- to C$_4$-hydroxyalkyl group which may be specified are a hydroxymethyl group, a 2-hydroxyethyl group, a 3-hydroxypropyl group or a 4-hydroxybutyl group. A 2-hydroxyethyl group is particularly preferred. A particularly preferred C$_2$- to C$_4$-polyhydroxyalkyl group is the 1,2-dihydroxyethyl group. According to the invention, examples of halogen atoms are F, Cl or Br atoms, Cl atoms are very particularly preferred. According to the invention, the other terms used are derived from the definitions given here. Examples of nitrogen-containing groups of the formula (E1) are in particular the amino groups, C$_1$- to C$_4$-monoalkylamino groups, C$_1$- to C$_4$-dialkylamino groups, C$_1$- to C$_4$-trialkylammonium groups, C$_1$- to C$_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, N-(4-amino-3-methyl-phenyl)-N-[3-(1H-imidizol-1-yl)propyl]amine and 5,8-diaminobenzo-1,4-dioxane and their physiologically compatible salts.

According to the invention, very particularly preferred p-phenylenediamine derivatives of the formula (E1) are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may also be preferred to use compounds which comprise at least two aromatic nuclei which are substituted by amino and/or hydroxyl groups as developer component.

Among the binuclear developer components which can be used in the coloring compositions according to the invention, specific mention may be made of the compounds which conform to the following formula (E2), and to their physiologically compatible salts:

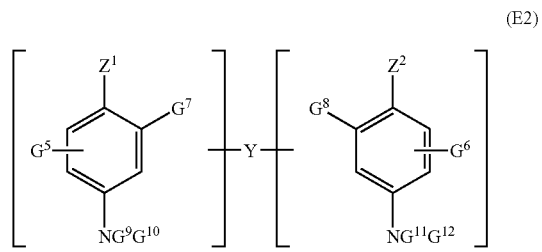

(E2)

where:
Z$^1$ and Z$^2$, independently of one another, are a hydroxyl or NH$_2$ radical, which is optionally substituted by a C$_1$- to C$_4$-alkyl radical, by a C$_1$- to C$_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring, which may be interrupted or terminated by one or more nitrogen-containing groups and/or one or more hetero atoms, such as oxygen, sulfur or nitrogen atoms, and may possibly be substituted by one or more hydroxyl radicals or C$_1$- to C$_8$-alkoxy radicals, or a direct bond, G$^5$ and G$^6$, independently of one another, are a hydrogen or halogen atom, a C$_1$- to C$_4$-alkyl radical, a C$_1$- to C$_4$-monohydroxyalkyl radical, a C$_2$- to C$_4$-polyhydroxyalkyl radical, a C$_1$- to C$_4$-aminoalkyl radical or a direct bond to the bridge Y, G$^7$, G$^8$, G$^9$, G$^{10}$, G$^{11}$ and G$^{12}$, independently of one another, are a hydrogen atom, a direct bond to the bridge Y or a C$_1$- to C$_4$-alkyl radical, with the proviso that the compounds of the formula (E2) comprise only one bridge Y per molecule.

According to the invention, the substituents used in formula (E2) are defined analogously to the above statements.

Preferred binuclear developer components of the formula (E2) are, in particular: N,N'-bis(β-hydroxyethyl)-N,N'-bis(4'-aminophenyl)-1,3-diaminopropan-2-ol, N,N'-bis(p-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane and 1,10-bis(2,5-diaminophenyl)-1,4,7,10-tetraoxadecane or one of their physiologically compatible salts.

In addition, it may be preferred according to the invention to use a p-aminophenol derivative or one of its physiologically compatible salts as developer component. Particular preference is given to p-aminophenol derivatives of the formula (E3)

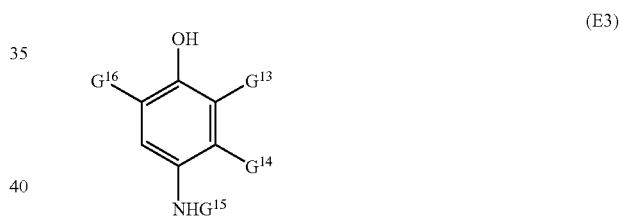

(E3)

where:
G$^{13}$ is a hydrogen atom, a halogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)alkoxy(C$_1$- to C$_4$)alkyl radical, a C$_1$- to C$_4$-aminoalkyl radical, a hydroxy(C$_1$- to C$_4$)alkylamino radical, a C$_1$- to C$_4$-hydroxyalkoxy radical, a C$_1$- to C$_4$-hydroxyalkyl(C$_1$- to C$_4$)aminoalkyl radical or a (di-C$_1$- to C$_4$-alkylamino)(C$_1$- to C$_4$)alkyl radical, and G$^{14}$ is a hydrogen or halogen atom, a C$_1$- to C$_4$-alkyl radical, a C$_1$- to C$_4$-monohydroxyalkyl radical, a C$_2$- to C$_4$-polyhydroxyalkyl radical, a (C$_1$- to C$_4$)alkoxy(C$_1$- to C$_4$)alkyl radical, a C$_1$- to C$_4$-aminoalkyl radical or a C$_1$- to C$_4$-cyanoalkyl radical, G$^{15}$ is hydrogen, a C$_1$- to C$_4$-alkyl radical, a C$_1$- to C$_4$-monohydroxyalkyl radical, a C$_2$- to C$_4$-polyhydroxyalkyl radical, a phenyl radical or a benzyl radical, and G$^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazolepyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese Laid-Open Specification JP 02019576 A2 or in the Laid-Open Specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

Preferred pyrazolepyrimidine derivatives are, in particular, the derivatives of pyrazole[1,5-a]pyrimidine of the following formula (E4) and tautomeric forms thereof if there is a tautomeric equilibrium:

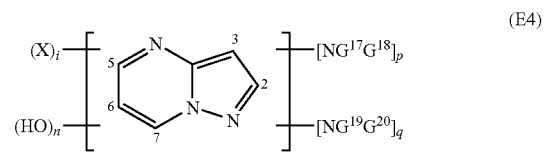

where:
G$^{17}$, G$^{18}$, G$^{19}$ and G$^{20}$, independently of one another, are a hydrogen atom, a C$_1$- to C$_4$-alkyl radical, an aryl radical, a C$_1$- to C$_4$-hydroxyalkyl radical, a C$_2$- to C$_4$-polyhydroxyalkyl radical, a (C$_1$- to C$_4$)alkoxy(C$_1$- to C$_4$)alkyl radical, a C$_1$- to C$_4$-aminoalkyl radical, which may optionally be protected by an acetylureido or a sulfonyl radical, a (C$_1$- to C$_4$)alkylamino(C$_1$- to C$_4$)alkyl radical, a di[(C$_1$- to C$_4$)alkyl](C$_1$- to C$_4$)aminoalkyl radical, where the dialkyl radicals optionally form a carbocycle or a heterocycle with 5 or 6 chain members, a C$_1$- to C$_4$-hydroxyalkyl or a di(C$_1$- to C$_4$)-[hydroxyalkyl](C$_1$- to C$_4$)aminoalkyl radical, the X radicals, independently of one another, are a hydrogen atom, a C$_1$- to C$_4$-alkyl radical, an aryl radical, a C$_1$- to C$_4$-hydroxyalkyl radical, a C$_2$- to C$_4$-polyhydroxyalkyl radical, a C$_1$- to C$_4$-aminoalkyl radical, a (C$_1$- to C$_4$)alkylamino(C$_1$- to C$_4$)alkyl radical, a di[(C$_1$- to C$_4$)alkyl](C$_1$- to C$_4$)aminoalkyl radical, where the dialkyl radicals optionally form a carbocycle or a heterocycle having 5 or 6 chain members, a C$_1$- to C$_4$-hydroxyalkyl or a di(C$_1$- to C$_4$-hydroxyalkyl)aminoalkyl radical, an amino radical, a C$_1$- to C$_4$-alkyl or di(C$_1$- to C$_4$-hydroxyalkyl)amino radical, a halogen atom, a carboxylic acid group or a sulfonic acid group, i has the value 0, 1, 2 or 3,
p has the value 0 or 1,
q has the value 0 or 1 and
n has the value 0 or 1, with the proviso that
the sum of p+q does not equal 0,
if p+q is 2, n has the value 0, and the groups NG$^{17}$G$^{18}$ and NG$^{19}$G$^{20}$ occupy positions (2,3); (5,6); (6,7); (3,5) or (3,7);
if p+q is 1, n has the value 1, and the groups NG$^{17}$G$^{18}$ (or NG$^{19}$G$^{20}$) and the group OH occupy positions (2,3); (5,6); (6,7); (3,5) or (3,7).

According to the invention, the substituents used in formula (E4) are defined analogously to the above statements.

If the pyrazole[1,5-a]pyrimidine of the above formula (E4) comprises a hydroxy group at one of positions 2, 5 or 7 of the ring system, there is a tautomeric equilibrium, which is represented, for example, in the following scheme:

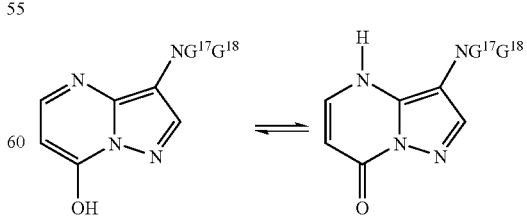

Among the pyrazole[1,5-a]pyrimidines of the above formula (E4), particular mention may be made of:
pyrazole[1,5-a]pyrimidine-3,7-diamine;

2,5-dimethylpyrazole[1,5-a]pyrimidine-3,7-diamine;
pyrazole[1,5-a]pyrimidine-3,5-diamine;
2,7-dimethylpyrazole[1,5-a]pyrimidine-3,5-diamine;
3-aminopyrazole[1,5-a]pyrimidin-7-ol;
3-aminopyrazole[1,5-a]pyrimidin-5-ol;
2-(3-aminopyrazole[1,5-a]pyrimidin-7-ylamino)ethanol;
2-(7-aminopyrazole[1,5-a]pyrimidin-3-ylamino)ethanol;
2-[(3-aminopyrazole[1,5-a]pyrimidin-7-yl)(2-hydroxyethyl)amino]ethanol;
2-[(7-aminopyrazole[1,5-a]pyrimidin-3-yl)(2-hydroxyethyl)amino]ethanol;
5,6-dimethylpyrazole[1,5-a]pyrimidine-3,7-diamine;
2,6-dimethylpyrazole[1,5-a]pyrimidine-3,7-diamine;
3-amino-7-dimethylamino-2,5-dimethylpyrazole[1,5-a]pyrimidine;

and their physiologically compatible salts and their tautomeric forms if a tautomeric equilibrium is present.

As described in the literature, the pyrazole[1,5-a]pyrimidines of the above formula (E4) can be prepared by cyclization starting from an aminopyrazole or from hydrazine.

In a further preferred embodiment, the colorants according to the invention comprise at least one coupler component.

The coupler components used are usually m-phenylenediamine derivatives, naphthols, resorcinol and resorcinol derivatives, pyrazolones and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,4-dichloro-3-aminophenol, 1,3-bis(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Coupler components preferred according to the invention are m-aminophenol and derivatives thereof, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-[3-morpholin-4-ylphenyl)amino]ethanol, 3-amino-4-(2-methoxyethoxy)-5-methylphenylamine and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene, and physiologically compatible salts thereof.

Coupler components which are particularly preferred according to the invention are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethyl resorcinol and 2,6-dihydroxy-3,4-dimethylpyridine.

The colorants according to the invention comprise the developer components and also the coupler components preferably in an amount of from 0.005 to 20% by weight, preferably 0.1 to 5% by weight, in each case based on the total oxidation colorant. Here, developer components and coupler components are generally used in approximately molar amounts relative to one another. Although the molar use has proven expedient, a certain excess of individual oxidation dye precursors is not disadvantageous, meaning that developer components and coupler components may be present in a molar ratio of from 1:0.5 to 1:3, in particular 1:1 to 1:2.

In a further embodiment of the present invention, the colorants comprise, as dye precursor (DP), at least one precursor of a nature-analogous dye. The precursors of nature-analogous dyes used are preferably those indoles and indolines which have at least one hydroxy or amino group, preferably as substituents on the six-membered ring. These groups can carry further substituents, e.g. in the form of an etherification or esterification of the hydroxy group or an alkylation of the amino group. In a second preferred embodiment, the colorants comprise at least one indole and/or indoline derivative.

Particularly well suited as precursors of nature-analogous hair dyes are derivatives of the 5,6-dihydroxyindoline of the formula (IIa),

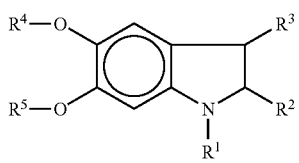

(IIa)

in which, independently of one another, $R^1$ is hydrogen, a $C_1$-$C_4$-alkyl group or a $C_1$-$C_4$-hydroxyalkyl group, $R^2$ is hydrogen or a —COOH group, where the —COOH group can also be present as a salt with a physiologically compatible cation, $R^3$ is hydrogen or a $C_1$-$C_4$-alkyl group, $R^4$ is hydrogen, a $C_1$-$C_4$-alkyl group or a group —CO—$R^6$, in which $R^6$ is a $C_1$-$C_4$-alkyl group, and $R^5$ is one of the groups given under $R^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline.

Exceptionally suitable precursors of nature-analogous hair dyes are also derivatives of the 5,6-dihydroxyindole of the formula (IIb),

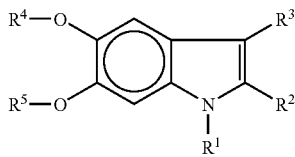

(IIb)

in which, independently of one another, $R^1$ is hydrogen, a $C_1$-$C_4$-alkyl group or a $C_1$-$C_4$-hydroxyalkyl group, $R^2$ is hydrogen or a —COOH group, where the —COOH group may also be present as a salt with a physiologically compatible cation, $R^3$ is hydrogen or a $C_1$-$C_4$-alkyl group, $R^4$ is hydrogen, a $C_1$-$C_4$-alkyl group or a group —CO—$R^6$, in which $R^6$ is a $C_1$-$C_4$-alkyl group, and $R^5$ is one of the groups given under $R^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is given to N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be used in the colorants according to the invention either as free bases or in the form of their physiologically compatible salts with inorganic or organic acids, e.g. the hydrochlorides, the sulfates and hydrobromides. The indole or indoline derivatives are usually present in these in amounts of 0.05-10% by weight, preferably 0.2-5% by weight.

In a further embodiment, it may be preferred according to the invention to use the indoline or indole derivative in colorants in combination with at least one amino acid or an oligopeptide. The amino acid is advantageously an alpha-amino acid; very particularly preferred alpha-amino acids are arginine, ornithine, lysine, serine and histidine, in particular arginine.

The *moringa* extract according to the invention has also proven to be particularly suitable for colorations based on direct dyes. Besides, or instead of, the dye precursor(s) according to the invention, the colorants according to the invention can therefore comprise one or more direct dyes in a further preferred embodiment of the present invention. The direct dyes are preferably chosen from the nitrophenylenediamines, the nitroaminophenols, the azo dyes, the anthraquinones or the indophenols.

Particularly preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, it may be preferred according to the invention for the agents to comprise at least one cationic direct dye. Particular preference is given here to (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which comprise at least one heterocycle which has at least one quaternary nitrogen atom, as are specified, for example, in EP-A2-998 908, which is hereby incorporated explicitly by reference, in claims 6 to 11.

Preferred cationic direct dyes of group (c) are, in particular, the following compounds:

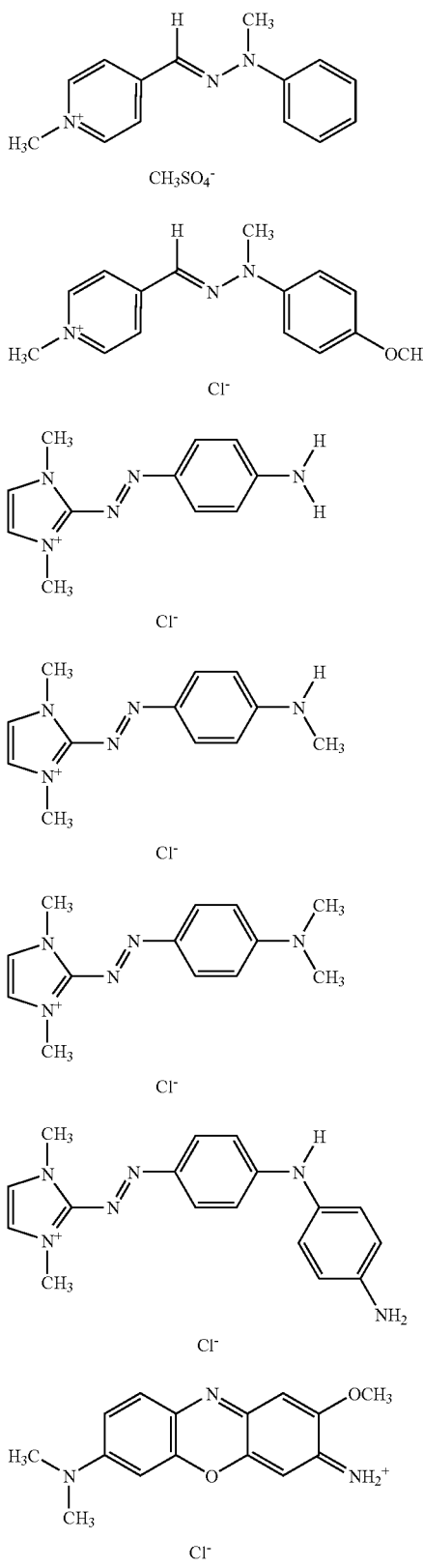

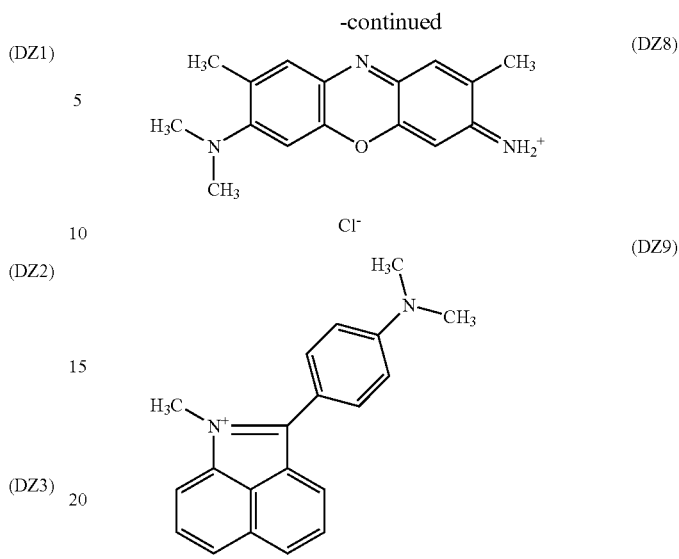

The compounds of the formulae (DZ1), (DZ3) and (DZ5), which are also known under the names Basic Yellow 87, Basic Orange 31 and Basic Red 51, are very particularly preferred cationic direct dyes of group (c).

The cationic direct dyes which are sold under the trade name Arianor® are likewise very particularly preferred cationic direct dyes according to the invention.

In addition, the preparations according to the invention can also comprise direct dyes which occur in nature, as are present, for example, in henna red, henna neutral, henna black, camomile blossom, sandalwood, black tea, buckthorn bark, sage, logwood, madder root, catechu, sedre and alkanna root.

The agents according to the invention comprise the direct dyes preferably in an amount of from 0.01 to 20% by weight, based on the total application preparation.

It is not necessary for the oxidation dye precursors or the direct dyes to each constitute uniform compounds. Rather, it is possible that, as a result of the preparation processes for the individual dyes, further components are present in minor amounts in the hair colorants according to the invention provided these do not adversely affect the coloring result, or have to be excluded for other reasons, e.g. toxicological reasons.

With regard to the dyes which can be used in the hair colorants and tints according to the invention, reference is also made expressly to the monograph by Ch. Zviak, The Science of Hair Care, chapter 7 (pages 248-250; direct dyes), and chapter 8, pages 264-267; oxidation dye precursors), published as volume 7 of the "Dermatology" series (editors: Ch. Culnan and H. Maibach), Verlag Marcel Dekker Inc., New York, Basle, 1986, and the "European Inventory of Cosmetic Raw Materials", published by the European Community, available in diskette form from the Bundesverband Deutscher Industrie- und Handelsunternehmen für Arzneimittel, Reformwaren und Körperpflegemittel e.V., Mannheim.

In a second embodiment of the present invention, the agents comprise at least one peroxo compound as color-modifying active ingredient. These agents are usually termed bleaches.

For bleaching human hair—particularly for strand application—solid or paste-like preparations containing solid peroxo compounds are usually mixed directly prior to application with a dilute hydrogen peroxide solution. This mixture is then applied to the hair and rinsed out again after a certain contact time.

The solid peroxo compounds usually do not constitute addition products of hydrogen peroxide onto other components. The choice of this peroxo compound is in principle not subject to limitations; customary peroxo compounds known to the person skilled in the art are, for example, ammonium peroxydisulfate, potassium peroxydisulfate, sodium peroxydisulfate, ammonium persulfate, potassium persulfate, sodium persulfate, potassium peroxydiphosphate, percarbonates, such as magnesium percarbonate, and peroxides such as barium peroxide. Of these peroxo compounds, which can also be used in combination, the inorganic compounds are preferred according to the invention. Particular preference is given to the peroxydisulfates, in particular ammonium peroxydisulfate.

The peroxo compounds are present in the agents according to the invention preferably in amounts of 5-30% by weight, in particular in amounts of 8-20% by weight.

As a further important component, bleaches comprise an alkalinizing agent which serves to establish the alkaline pH of the application mixture.

According to the invention, use may be made of the customary alkalinizing agents likewise known to the person skilled in the art for bleaches, such as ammonium, alkali metal and alkaline earth metal hydroxides, carbonates, hydrogencarbonates, hydroxycarbonates, silicates, in particular metasilicates, and alkali metal phosphates. In a preferred embodiment, the bleaches according to the invention comprise at least two different alkalinizing agents. In this connection, mixtures of, for example, a metasilicate and a hydroxycarbonate may be preferred.

Bleaches comprise alkalinizing agents preferably in amounts of 5-25% by weight, in particular 10-20% by weight.

As further important component, bleaches usually comprise hydrogen peroxide or a solid addition compound of hydrogen peroxide onto inorganic or organic compounds, such as, for example, sodium perborate, sodium percarbonate, sodium percarbamide, polyvinylpyrrolidone, urea peroxide and melamine peroxide.

The concentration of this hydrogen peroxide solution is on the one hand determined by the legal stipulations and on the other hand by the desired effect; as a rule, 6 to 12% strength solutions in water are used. The quantitative ratios of the component which comprises the peroxo compound to the hydrogen peroxide solution are here usually in the range 1:1 to 1:2, with an excess of hydrogen peroxide solution being chosen particularly if a not too marked bleaching effect is desired.

In addition, it has proven to be advantageous if the color-modifying agents according to the invention comprise at least one care substance.

Within the scope of a first preferred embodiment, the color-modifying agent according to the invention comprises at least one cationic surfactant as care substance.

According to the invention, preference is given to cationic surfactants of the quaternary ammonium compound type, of the esterquat type and of the amidoamine type. Preferred quaternary ammonium compounds are ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the abovementioned surfactants preferably have 10 to 18 carbon atoms.

Ester quats are known substances which contain both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, and N,N-bis(2-palmitoyloxyethyl)dimethylammonium chloride, and Dehyquart® F-75, Dehyquart® C-4046, Dehyquart® L80 and Dehyquart® AU-35 are examples of such ester quats.

The alkylamidoamines are usually prepared by amidation of natural or synthetic fatty acids and fatty acid cuts with dialkylaminoamines. One compound from this group of substances that is particularly suitable according to the invention is the stearamidopropydimethylamine commercially available under the name Tegoamid® S 18.

Further cationic surfactants suitable according to the invention are the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are sold, for example, by Mona under the trade names Phospholipid EFA®, Phospholipid PTC® and Phospholipid SV®.

The cationic surfactants are present in the agents used according to the invention preferably in amounts of from 0.05 to 10% by weight, based on the total application preparation. Amounts of from 0.1 to 5% by weight are particularly preferred.

Within the scope of a second preferred embodiment of the present invention, the color-modifying agents comprise at least one care polymer as care substance.

A first group of the care polymers are the cationic polymers. According to the invention, cationic polymers are to be understood as meaning polymers which, in the main chain and/or side chain, have a group which may be "temporarily" or "permanently" cationic. According to the invention, the term "permanently cationic" is used to refer to those polymers which have a cationic group irrespective of the pH of the composition. These are generally polymers which contain a quaternary nitrogen atom, for example in the form of an ammonium group. Preferred cationic groups are quaternary ammonium groups. In particular, those polymers in which the quaternary ammonium groups are bonded via a $C_{1-4}$ hydrocarbon group to a polymer main chain constructed from acrylic acid, methacrylic acid or derivatives thereof have proven to be particularly suitable.

Homopolymers of the general formula (G1-I)

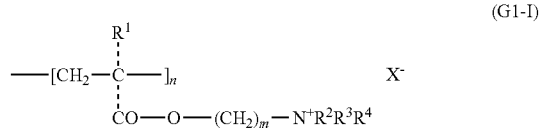

in which $R^1$=—H or —$CH_3$, $R^2$, $R^3$ and $R^4$, independently of one another, are chosen from $C_{1-4}$-alkyl, -alkenyl or -hydroxyalkyl groups, m=1, 2, 3 or 4, n is a natural number and $X^-$ is a physiologically compatible organic or inorganic anion, and copolymers consisting essentially of the monomer units listed in formula (G1-I), and nonionogenic monomer units, are particularly preferred cationic polymers. Among these polymers, preference is given according to the invention to those for which at least one of the following conditions applies:

$R^1$ is a methyl group $R^2$, $R^3$ and $R^4$ are methyl groups m has the value 2.

Suitable physiologically compatible counterions $X^-$ are, for example, halide ions, sulfate ions, phosphate ions, methosulfate ions, and organic ions, such as lactate, citrate, tartrate and acetate ions. Preference is given to halide ions, in particular chloride.

A particularly suitable homopolymer is, if desired crosslinked, poly(methacryloyloxyethyltrimethylammonium chloride) with the INCI name Polyquaternium-37. The crosslinking can take place if desired with the help of polyolefinically unsaturated compounds, for example divinylbenzene, tetraallyloxyethane, methylenebisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylenebisacrylamide is a preferred crosslinking composition.

The homopolymer is preferably used in the form of a nonaqueous polymer dispersion which should have a polymer fraction not below 30% by weight. Such polymer dispersions are commercially available under the names Salcare® SC 95 (about 50% polymer fraction, further components: mineral oil (INCI name: Mineral Oil) and tridecyl polyoxypropylene polyoxyethylene ether (INCI name: PPG-1-Trideceth-6)) and Salcare® SC 96 (about 50% polymer fraction, further components: mixture of diesters of propylene glycol with a mixture of caprylic acid and capric acid (INCI name: Propylene Glycol Dicaprylate/Dicaprate) and tridecyl polyoxypropylene polyoxyethylene ether (INCI name: PPG-1-Trideceth-6)).

Copolymers with monomer units according to formula (G1-I) comprise, as nonionogenic monomer units, preferably acrylamide, methacrylamide, $C_{1-4}$-alkyl acrylates and $C_{1-4}$-alkyl methacrylates. Among these nonionogenic monomers, particular preference is given to acrylamide. As in the case of the homopolymers described above, these copolymers too may be crosslinked. A copolymer preferred according to the invention is the crosslinked acrylamide-methacryloyloxyethyltrimethylammonium chloride copolymer. Such copolymers in which the monomers are present in a weight ratio of about 20:80 are commercially available as about 50% strength nonaqueous polymer dispersion under the name Salcare® SC 92.

Further preferred cationic polymers are, for example, quaternized cellulose derivatives, as are commercially available under the names Celquat® and Polymer JR®. The compounds Celquat® H 100, Celquat® L 200 and Polymer JR® 400 are preferred quaternized cellulose derivatives, cationic alkyl polyglycosides as in DE-C 44 13 686, cationized honey, for example the commercial product Honeyquat® 50, cationic guar derivatives, such as, in particular, the products sold under the trade names Cosmedia® Guar and Jaguar®, polysiloxanes with quaternary groups, such as, for example, the commercially available products Q2-7224 (manufacturer: Dow Corning; a stabilized trimethylsilylamodimethicone), Dow Corning® 929 emulsion (comprising a hydroxylamino-modified silicone, which is also referred to as amodimethicone), SM-2059 (manufacturer: General Electric), SLM-55067 (manufacturer: Wacker), and Abil®-Quat 3270 and 3272 (manufacturer: Th. Goldschmidt), diquaternary polydimethylsiloxanes, Quaternium-80), polymeric dimethyldiallylammonium salts and copolymers thereof with esters and amides of acrylic acid and methacrylic acid. The products commercially available under the names Merquat® 100 (poly(dimethyldiallylammonium chloride)) and Merquat® 550 (dimethyldiallylammonium chloride-acrylamide copolymer) are examples of such cationic polymers, copolymers of vinylpyrrolidone with quaternized derivatives of dialkylaminoalkyl acrylate and methacrylate, such as, for example, vinylpyrrolidone-dimethylaminoethyl methacrylate copolymers quaternized with diethyl sulfate. Such compounds are commercially available under the names Gafquat® 734 and Gafquat® 755, vinylpyrrolidone-vinylimidazolium methochloride copolymers, as are supplied under the names Luviquat® FC 370, FC 550, FC 905 and HM 552, quaternized polyvinyl alcohol, and the polymers known under the names Polyquaternium 2, Polyquaternium 17, Polyquaternium 18 and Polyquaternium 27 with quaternary nitrogen atoms in the polymer main chain.

As cationic polymers it is likewise possible to use the polymers known under the names Polyquaternium-24 (commercial product e.g. Quatrisoft® LM 200). According to the invention, it is likewise possible to use the copolymers of vinylpyrrolidone, as are obtainable as commercial products Copolymer 845 (manufacturer: ISP), Gaffix® VC 713 (manufacturer: ISP), Gafquat® ASCP 1011, Gafquat® HS 110, Luviquat® 8155 and Luviquat® MS 370.

Further cationic polymers according to the invention are the so-called "temporarily cationic" polymers. These polymers usually comprise an amino group which is present as quaternary ammonium group and thus in cationic form at certain pH values. Preference is given, for example, to chitosan and derivatives thereof, as are freely available commercially, for example, under the trade names Hydagen® CMF, Hydagen® HCMF, Kytamer® PC and Chitolam® NB/101.

Cationic polymers preferred according to the invention are cationic cellulose derivatives and chitosan and derivatives thereof, in particular the commercial products Polymer® JR 400, Hydagen® HCMF and Kytamer® PC, cationic guar derivatives, cationic honey derivatives, in particular the commercial product Honeyquat® 50, cationic alkyl polyglycosides as in DE-C 44 13 686 and polymers of the Polyquaternium-37 type.

In addition, cationized protein hydrolyzates are types of cationic polymers, where the parent protein hydrolyzate can originate from animal, for example from collagen, milk or keratin, from plant, for example from wheat, corn, rice, potatoes, soya or almonds, from marine life forms, for example from fish collagen or algae, or protein hydrolyzates obtained by biotechnological methods. The protein hydrolyzates on which the cationic derivatives according to the invention are based can be obtained from the corresponding proteins by a chemical, in particular alkaline or acidic, hydrolysis, by an enzymatic hydrolysis and/or a combination of both types of hydrolysis. The hydrolysis of proteins generally gives a protein hydrolyzate with a molecular weight distribution from about 100 daltons to several thousand daltons. Preference is given here to those cationic protein hydrolyzates whose parent protein moiety has a molecular weight of from 100 to 25 000 daltons, preferably 250 to 5000 daltons. In addition, cationic protein hydrolyzates are to be understood as meaning quaternized amino acids and mixtures thereof. The quaternization of the protein hydrolyzates or of the amino acids is often carried out using quaternary ammonion salts, such as, for example, N,N-dimethyl-N-(n-alkyl)-N-(2-hydroxy-3-chloro-n-propyl)ammonium halides. In addition, the cationic protein hydrolyzates can also be yet further derivatized. Typical examples of the cationic protein hydrolyzates and derivatives according to the invention which may be mentioned are the products specified under the INCI names in the "International Cosmetic Ingredient Dictionary and Handbook", (seventh edition 1997, The Cosmetic, Toiletry, and Fragrance Association 1101 17$^{th}$ Street, N.W., Suite 300, Washington, D.C. 20036-4702) and commercially available products: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryidimonium Hydroxypropyl Hydrolyzed Casein, Lauryidimonium Hydroxypropyl Hydrolyzed Collagen, Lauryldimonium Hydroxypropyl Hydrolyzed Keratin, Lauryidimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

Very particular preference is given to the plant-based cationic protein hydrolyzates and derivatives.

Further care polymers which can be used according to the invention are the amphoteric compounds specified in the British Laid-Open Specification 2 104 091, the European Laid-Open Specification 47 714, the European Laid-Open Specification 217 274, the European Laid-Open Specification 283 817 and the German Laid-Open Specification 28 17 369.

Preferably used amphoteric polymers are those polymers which consist essentially of (a) monomers with quaternary ammonium groups of the general formula (II),

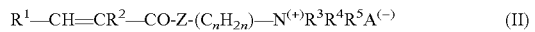

$$R^1\text{—}CH\text{=}CR^2\text{—}CO\text{-}Z\text{-}(C_nH_{2n})\text{—}N^{(+)}R^3R^4R^5A^{(-)} \quad \text{(II)}$$

in which $R^1$ and $R^2$, independently of one another, are hydrogen or a methyl group and $R^3$, $R^4$ and $R^5$, independently of one another, are alkyl groups having 1 to 4 carbon atoms, Z is an NH group or an oxygen atom, n is an integer from 2 to 5 and $A^{(-)}$ is the anion of an organic or inorganic acid, and (b) monomeric carboxylic acids of the general formula (III),

$$R^6\text{—}CH\text{=}CR^7\text{—}COOH \quad \text{(III)}$$

in which $R^6$ and $R^7$, independently of one another, are hydrogen or methyl groups.

According to the invention, these compounds can either be used directly or in salt form, which is obtained by neutralization of the polymers, for example with an alkali metal hydroxide. For the details of the preparation of these polymers, reference is made expressly to the contents of the German Laid-Open Specification 39 29 973. Very particular preference is given to using those polymers in which monomers of type (a) are used, in which $R^3$, $R^4$ and $R^5$ are methyl groups, Z is an NH group and $A^{(-)}$ is a halide, methoxysulfate or ethoxysulfate ion; acrylamidopropyltrimethylammonium chloride is a particularly preferred monomer (a). The monomer (b) used for the specific polymers is preferably acrylic acid.

The color-modifying agents according to the invention comprise the cationic polymers preferably in an amount of from 0.01 to 5% by weight, in particular in an amount of from 0.1 to 2% by weight, in each case based on the total application preparation.

Within the scope of a third preferred embodiment, the color-modifying agents according to the invention comprise at least one UV filter. The UV filters suitable according to the invention are not subject to any general limitations with regard to their structure and their physical properties. Rather, all UV filters which can be used in the cosmetics sector and whose absorption maxima is in the UVA (315-400 nm) region, in the UVB (280-315 nm) region or in the UVC (<280 nm) region are suitable. UV filters with an absorption maximum in the UVB region, in particular in the range from about 280 to about 300 nm, are particularly preferred.

The UV filters preferred according to the invention can be chosen, for example, from substituted benzophenones, p-aminobenzoic acid esters, diphenylacrylic acid esters, cinnamic acid esters, salicylic acid esters, benzimidazoles and o-aminobenzoic acid esters.

Examples of UV filters which can be used according to the invention are 4-aminobenzoic acid, N,N,N-trimethyl-4-(2-oxoborn-3-ylidenemethyl)aniline methylsulfate, 3,3,5-trimethylcyclohexyl salicylate (homosalate), 2-hydroxy-4-methoxybenzophenone (benzophenone-3; Uvinul® M 40, Uvasorb® MET, Neo Heliopan® BB, Eusolex® 4360), 2-phenylbenzimidazole-5-sulfonic acid and the potassium, sodium and triethanolamine salts thereof (phenylbenzimidazolesulfonic acid; Parsol® DHS; Neo Heliopan® Hydro), 3,3'-(1,4-phenylenedimethylene)bis(7,7-dimethyl-2-oxobicyclo[2.2.1]hept-1-ylmethanesulfonic acid) and salts thereof, 1-(4-tert-butylphenyl)-3-(4-methoxyphenyl)propane-1,3-dione (butylmethoxydibenzoylmethane; Parsol® 1789, Eusolex® 9020), α-(2-oxoborn-3-ylidene)toluene-4-sulfonic acid and salts thereof, ethoxylated ethyl 4-aminobenzoate (PEG-25 PABA; Uvinul® P 25), 2-ethylhexyl 4-dimethylaminobenzoate (octyl dimethyl PABA; Uvasorb® DMO, Escalol® 507, Eusolex® 6007), 2-ethylhexyl salicylate (octyl salicylate; Escalol® 587, Neo Heliopan® OS, Uvinul® O18), isopentyl 4-methoxycinnamate (isoamyl p-methoxycinnamate; Neo Heliopan® E 1000), 2-ethylhexyl 4-methoxycinnamate (octyl methoxycinnamate; Parsol® MCX, Escalol® 557, Neo Heliopan® AV), 2-hydroxy-4-methoxybenzophenone-5-sulfonic acid and the sodium salt thereof (benzophenone-4; Uvinol® MS 40; Uvasorb® S 5), 3-(4'-methylbenzylidene)-D,L-camphor (4-methylbenzylidenecamphor; Parsol® 5000, Eusolex® 6300), 3-benzylidenecamphor, 4-isopropylbenzyl salicylate, 2,4,6-trianilino(p-carbo-2'-ethylhexyl-1'-oxy)-1,3,5-triazine, 3-imidazol-4-ylacrylic acid and the ethyl ester thereof, polymers of N-{(2 and 4)-[2-oxoborn-3-ylidenemethyl)benzyl}acrylamide, 2,4-dihydroxybenzophenone (benzophenone-1; Uvasorb® 20H, Uvinol® 400), 1,1'-diphenylacrylonitrile acid 2-ethylhexyl ester (octocrylene; Eusolex® OCR, Neo Heliopan® Type 303, Univul® N 539 SG), menthyl o-aminobenzoate (menthyl anthranilate; Neo Heliopan® MA), 2,2',4,4'-tetrahydroxybenzophenone (benzophenone-2; Uvinul® D-50), 2,2'-dihydroxy-4,4'-dimethoxybenzophenone (benzophenone-6), 2,2'-dihydroxy-4,4'-dimethoxybenzophenone-5 sodium sulfonate and 2'-ethylhexyl 2-cyano-3,3-diphenylacrylate. Preference is given to 4-aminobenzoic acid, N,N,N-trimethyl-4-(2-oxoborn-3-ylidenemethyl)aniline methylsulfate, 3,3,5-trimethylcyclohexyl salicylate, 2-hydroxy-4-methoxybenzophenone, 2-phenylbenzimidazole-5-sulfonic acid and the potassium, sodium and triethanolamine salts thereof, 3,3'-(1,4-phenylenedimethylene)bis(7,7-dimethyl-2-oxobicyclo[2.2.1]hept-1-ylmethanesulfonic acid) and salts thereof, 1-(4-tert-butylphenyl)-3-(4-methoxyphenyl)propane-1,3-dione, α-(2-oxoborn-3-ylidene)toluene-4-sulfonic acid and salts thereof, ethoxylated ethyl 4-aminobenzoate, 2-ethylhexyl 4-dimethylaminobenzoate, 2-ethylhexyl salicylate, isopentyl 4-methoxycinnamate, 2-ethylhexyl 4-methoxycinnamate, 2-hydroxy-4-methoxybenzophenone-5-sulfonic acid and the sodium salt thereof, 3-(4'-methylbenzylidene)-D,L-camphor, 3-benzylidenecamphor, 4-isopropylbenzyl salicylate, 2,4,6-trianilino(p-carbo-2'-ethylhexyl-1'-oxy)-1,3,5-triazine, 3-imidazol-4-ylacrylic acid and the ethyl ester thereof, polymers of N-{(2 and 4)-[2-oxoborn-3-ylidenemethyl]benzyl}acrylamide. According to the invention, very particular preference is given to 2-hydroxy-4-methoxybenzophenone, 2-phenylbenzimidazole-5-sulfonic acid and the potassium, sodium and triethanolamine salts thereof, 1-(4-tert-butylphenyl)-3-(4-methoxyphenyl) propane-1,3-dione, 2-ethylhexyl 4-methoxycinnamate and 3-(4'-methylbenzylidene)-D,L-camphor.

Preference is given to those UV filters whose molar absorbance coefficient is at the absorption maximum above 15 000, in particular above 20 000.

Furthermore, it has been found that for structurally similar UV filters, in many cases the water-insoluble compound within the scope of the teaching according to the invention has the higher effect compared to those water-soluble compounds which differ from it by virtue of one or more additionally ionic groups. For the purposes of the invention, water-insoluble UV filters are to be understood as meaning those which dissolve in water at 20° C. to not more than 1% by weight, in particular to not more than 0.1% by weight. Furthermore, these compounds should be soluble in customary cosmetic oil components at room temperature to at least 0.1% by weight, in particular to at least 1% by weight. The use of water-insoluble UV filters can therefore be preferred according to the invention.

According to a further embodiment of the invention, preference is given to those UV filters which have a cationic group, in particular a quaternary ammonium group.

These UV filters have the general structure U-Q.

The structural moiety U is here a group which absorbs UV rays. This group can in principle be derived from the known abovementioned UV filters which can be used in the cosmetics sector by replacing one group, generally a hydrogen atom, of the UV filter with a cationic group Q, in particular with a quaternary amino function.

Compounds from which the structural moiety U can be derived are, for example,
substituted benzophenones,
p-aminobenzoic acid esters,
diphenylacrylic acid esters,
cinnamic acid esters,
salicylic acid esters,
benzimidazoles and
o-aminobenzoic acid esters.

Structural moieties U which derive from cinnamamide or N,N-dimethylaminobenzamide are preferred according to the invention.

The structural moieties U can in principle be chosen so that the absorption maximum of the UV filters can be both in the UVA (315-400 nm) region, or in the UVB (280-315 nm) region or in the UVC (<280 nm) region. UV filters with an absorption maximum in the UVB region, in particular in the range from about 280 to about 300 nm, are particularly preferred.

In addition, the structural moiety U is chosen, also depending on structural moiety Q, preferably such that the molar absorbance coefficient of the UV filter at the absorption maximum is above 15 000, in particular above 20 000.

The structural moiety Q comprises, as cationic group, preferably a quaternary ammonium group. This quaternary ammonium group can in principle be joined directly to the structural moiety U, meaning that the structural moiety U is one of the four substituents of the positively charged nitrogen atom. However, one of the four substituents on the positively charged nitrogen atom is preferably a group, in particular an alkylene group having 2 to 6 carbon atoms, which functions as linkage between the structural moiety U and the positively charged nitrogen atom.

Advantageously, the group Q has the general structure —$(CH_2)_x$—$N^+R^1R^2R^3X^-$, in which x is an integer from 1 to 4, $R^1$ and $R^2$, independently of one another, are $C_{1-4}$-alkyl groups, $R^3$ is a $C_{1-22}$-alkyl group or a benzyl group and $X^-$ is a physiologically compatible anion. Within the context of this general structure, x is preferably 3, $R^1$ and $R^2$ are in each case a methyl group and $R^3$ is either a methyl group or a saturated or unsaturated, linear or branched hydrocarbon chain having 8 to 22, in particular 10 to 18, carbon atoms.

Physiologically compatible anions are, for example, inorganic anions, such as halides, in particular chloride, bromide and fluoride, sulfate ions and phosphate ions, and organic anions, such as lactate, citrate, acetate, tartrate, methosulfate and tosylate.

Two preferred UV filters with cationic groups are the commercially available compounds cinnamic acid amidopropyltrimethylammonium chloride (Incroquat® UV-283) and dodecyldimethylaminobenzamidopropyldimethylammonium tosylate (Escalol® HP 610).

The teaching according to the invention of course also includes the use of a combination of two or more UV filters. Within the scope of this embodiment, the combination of at least one water-insoluble UV filter with at least one UV filter with a cationic group is preferred.

The UV filters are present in the agents according to the invention usually in amounts of 0.01-5% by weight, based on the total application preparation. Amounts of 0.1-2.5% by weight are preferred.

Within the scope of a fourth preferred embodiment, the color-modifying agents according to the invention comprise, as care substance, at least one vitamin, one provitamin, one vitamin precursor, and one of their derivatives.

In this connection, preference is given according to the invention to those vitamins, provitamins and vitamin precursors which are usually assigned to the groups A, B, C, E, F and H.

The group of the substances referred to as vitamin A includes retinol (vitamin $A_1$) and 3,4-didehydroretinol (vitamin $A_2$). β-Carotene is the provitamin of retinol. Suitable as vitamin A component are, according to the invention, for example vitamin A acid and esters thereof, vitamin A aldehyde and vitamin A alcohol, and esters thereof, such as the palmitate and the acetate. The preparations used according to the invention comprise the vitamin A component preferably in amounts of 0.05-1% by weight, based on the total application preparation.

The vitamin B group or the vitamin B complex includes, inter alia, vitamin $B_1$ (thiamine)

vitamin $B_2$ (riboflavin)

vitamin $B_3$. This name often covers the compounds nicotinic acid and nicotinamide (niacinamide). According to the invention, preference is given to nicotinamide, which is present in the agents according to the invention preferably in amounts of from 0.05 to 1% by weight, based on the total application preparation.

Vitamin $B_5$ (pantothenic acid, panthenol and pantolactone). Within the scope of this group, preference is given to using panthenol and/or pantolactone. Derivatives of panthenol which can be used according to the invention are, in particular, the esters and ethers of panthenol, and cationically derivatized panthenols. Individual representatives are, for example, panthenol triacetate, panthenol monoethyl ether and its monoacetate, and the cationic panthenol derivatives disclosed in WO 92/13829. The specified compounds of the vitamin $B_5$ type are present in the agents according to the invention preferably in amounts of 0.05-10% by weight, based on the total application preparation. Amounts of 0.1-5% by weight are particularly preferred.

Vitamin $B_6$ (pyridoxine and pyridoxamine and pyridoxal). The specified compounds of the vitamin $B_6$ type are present in the agents according to the invention preferably in amounts of 0.01-5% by weight, based on the total application preparation. Amounts of 0.05-1% by weight are particularly preferred.

Vitamin C (ascorbic acid). Vitamin C is used in the agents used according to the invention preferably in amounts of from 0.1 to 3% by weight, based on the total application preparation. Use in the form of the palmitic acid ester, the glucosides or phosphates may be preferred. Use in combination with tocopherols may likewise be preferred.

Vitamin E (tocopherols, in particular α-tocopherol). Tocopherol and its derivatives, which include, in particular, the esters, such as the acetate, the nicotinate, the phosphate and the succinate, are present in the agents according to the invention preferably in amounts of 0.05-1% by weight, based on the total application preparation.

Vitamin F. The term "vitamin F" is usually understood as meaning essential fatty acids, in particular linoleic acid, linolenic acid and arachidonic acid.

Vitamin H. Vitamin H is the term used to refer to the compound (3aS,4S,6aR)-2-oxohexahydrothienol[3,4-d]imidazole-4-valeric acid, for which, however, the trivial name biotin has meanwhile caught on. Biotin is present in the agents according to the invention preferably in amounts of from 0.0001 to 1.0% by weight, in particular in amounts of from 0.001 to 0.01% by weight, in each case based on the total application preparation.

Preferably, the color-modifying agents according to the invention comprise vitamins, provitamins and vitamin precursors from the groups A, B, C, E and H.

Panthenol, pantolactone, pyridoxine and its derivatives, and also nicotinamide and biotin are particularly preferred.

Within the scope of a fifth preferred embodiment, the color-modifying agents according to the invention comprise at least one plant extract.

These extracts are usually prepared by extracting the whole plant. However, in individual cases, it may also be preferred to prepare the extracts exclusively from flowers and/or leaves of the plant.

With regard to the plant extracts preferred according to the invention, reference is made in particular to the extracts which are listed in the table starting on page 44 of the 3rd edition of the introduction to the ingredients declaration of cosmetic compositions, published by the Industrieverband Körperpflege- und Waschmittel e.V. (IKW), Frankfurt.

According to the invention, the extracts from green tea, oak bark, stinging nettle, hamamelis, hops, henna, camomile, burdock, horsetail, hawthorn, linden blossom, almond, aloe vera, spruce needle, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, meristem, ginseng and ginger root in particular are preferred.

Particular preference is given to the extracts from green tea, oak bark, stinging nettle, hamamelis, hops, camomile, burdock, horsetail, linden blossom, almond, aloe vera, coconut, mango, apricot, lemon, wheat, kiwi, melon, orange, grapefruit, sage, rosemary, birch, lady's smock, wild thyme, yarrow, restharrow, meristem, ginseng and ginger root.

Of very particular suitability are the extracts from green tea, almond, aloe vera, coconut, mango, apricot, lemon, wheat, kiwi and melon.

Extractants for producing the specified plant extracts which may be used are water, alcohols and mixtures thereof. Among the alcohols, preference is given here to lower alcohols, such as ethanol and isopropanol, but in particular polyhydric alcohols, such as ethylene glycol and propylene glycol, both as the sole extractant and also in a mixture with water. Plant extracts based on water/propylene glycol in the ratio 1:10 to 10:1 have proven to be particularly suitable.

According to the invention, the plant extracts can be used either in pure form or in dilute form. If they are used in dilute form, they usually comprise about 2-80% by weight of active substance and, as solvent, the extractant or extractant mixture used during their isolation.

In addition, it may be preferred to use mixtures of two or more, in particular of two, different plant extracts in the color-modifying agents according to the invention.

Within the scope of a sixth embodiment, the color-modifying agents according to the invention comprise at least one carboxylic acid as care substance.

Particularly short-chain carboxylic acids may be advantageous for the purposes of the invention. For the purposes of the invention, short-chain carboxylic acids and derivatives thereof are understood as meaning carboxylic acids which may be saturated or unsaturated and/or straight-chain or branched or cyclic and/or aromatic and/or heterocyclic and have a molecular weight of less than 750. For the purposes of the invention, saturated or unsaturated straight-chain or branched carboxylic acids with a chain length of from 1 to 16 carbon atoms in the chain may be preferred, very particular preference being given to those with a chain length of from 1 to 12 carbon atoms in the chain.

For the purposes of the invention, the short-chain carboxylic acids can have one, two, three or more carboxy groups. For the purposes of the invention, preference is given to carboxylic acids with two or more carboxy groups, in particular di- and tricarboxylic acids. The carboxy groups may be present completely or in part as ester, acid anhydride, lactone, amide, imidic acid, lactam, lactim, dicarboximide, carbohydrazide, hydrazone, hydroxam, hydroxime, amidine, amide oxime, nitrile, phosphonic or phosphate ester. The carboxylic acids according to the invention can of course be substituted along the carbon chain or the ring backbone. The substituents of the carboxylic acids according to the invention are to include, for example, $C_1$-$C_8$-alkyl, $C_2$-$C_8$-alkenyl, aryl, aralkyl and aralkenyl, hydroxymethyl, $C_2$-$C_8$-hydroxyalkyl, $C_2$-$C_8$-hydroxyalkenyl, aminomethyl, $C_2$-$C_8$-aminoalkyl, cyano, formyl, oxo, thioxo, hydroxy, mercapto, amino, carboxy or imino groups. Preferred substituents are $C_1$-$C_8$-alkyl, hydroxymethyl, hydroxy, amino and carboxy groups. Particular preference is given to substituents in the a position. Very particularly preferred substituents are hydroxy, alkoxy and amino groups, where the amino function may optionally be further substituted by alkyl, aryl, aralkyl and/or alkenyl radicals. Furthermore, likewise preferred carboxylic acid derivatives are the phosphonic and phosphate esters.

Examples of carboxylic acids according to the invention which may be mentioned are formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluoyl acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-naphthalenepentaacetic acid, malonaldehyde acid, 4-hydroxyphthalamide acid, 1-pyrazolecarboxylic acid, gallic acid or propanetricarboxylic acid, a dicarboxylic acid chosen from the group which is formed by compounds of the general formula (N-I),

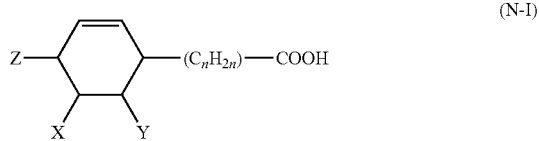

in which Z is a linear or branched alkyl or alkenyl group having 4 to 12 carbon atoms, n is a number from 4 to 12, and one of the two groups X and Y is a COOH group and the other is hydrogen or a methyl or ethyl radical, dicarboxylic acids of the general formula (N-I) which additionally also carry 1 to 3 methyl or ethyl substituents on the cyclohexene ring, and dicarboxylic acids which form from the dicarboxylic acids according to formula (N-I) formally by addition of a molecule of water onto the double bond in the cyclohexene ring.

Dicarboxylic acids of the formula (N-I) are known in the literature. Thus, for example, a preparation process is given, for example, in U.S. Pat. No. 3,753,968.

The dicarboxylic acids of the formula (N-I) can be prepared, for example, by reacting polyunsaturated dicarboxylic acids with unsaturated monocarboxylic acids in the form of a Diels-Alder cyclization. The process usually starts from a polyunsaturated fatty acid as dicarboxylic acid component. Preference is given to the linoleic acid obtainable from natural fats and oils. As monocarboxylic acid component, preference is given in particular to acrylic acid, but also, for example, to methacrylic acid and crotonic acid. Usually, in reactions according to Diels-Alder, isomer mixtures are formed in which one component is present in excess. According to the invention, these isomer mixtures can be used just as much as the pure compounds.

Besides the preferred dicarboxylic acids according to formula (N-I), according to the invention it is also possible to use those dicarboxylic acids which differ from the compounds according to formula (N-I) by 1 to 3 methyl or ethyl substituents on the cyclohexyl ring or are formed from these compounds formally by adding a molecule of water onto the double bond of the cyclohexene ring.

The dicarboxylic acid (mixture) which forms by reacting linoleic acid with acrylic acid has proven particularly advantageous according to the invention. This is a mixture of 5- and 6-carboxy-4-hexyl-2-cyclohexene-1-octanoic acid. Such compounds are commercially available under the names Westvaco Diacid® 1550 and Westvaco Diacid® 1595 (manufacturer: Westvaco).

Besides the short-chain carboxylic acids according to the invention themselves listed above by way of example, it is also possible to use their physiologically compatible salts according to the invention. Examples of such salts are the alkali metal, alkaline earth metal, zinc salts and also ammonium salts, which, for the purposes of the present application, are also understood as meaning the mono-, di- and trimethyl-, -ethyl- and -hydroxyethylammonium salts. However, for the purposes of the invention, very particular preference may be given to using acids neutralized with alkaline-reacting amino acids, such as, for example, arginine, lysine, ornithine and histidine. Furthermore, it may be preferred, for formulation reasons, to choose the carboxylic acid from the water-soluble representatives, in particular the water-soluble salts.

Furthermore, it is preferred according to the invention to use 2-pyrrolidinone-5-carboxylic acid and derivatives thereof as carboxylic acid. Particular preference is given to the sodium, potassium, calcium, magnesium or ammonium salts in which the ammonium ion carries one to three $C_1$- to $C_4$-alkyl groups besides hydrogen. The sodium salt is very particularly preferred. The amounts used in the agents according to the invention are 0.05 to 10% by weight, based on the total application preparation, particularly preferably 0.1 to 5% by weight, and in particular 0.1 to 3% by weight.

In addition, it is preferred according to the invention to use hydroxycarboxylic acids and here in turn, in particular, the dihydroxy-, trihydroxy- and polyhydroxycarboxylic acids, and the dihydroxy-, trihydroxy- and polyhydroxy- di-, tri- and polycarboxylic acids. In this connection, it has been found that, besides the hydroxycarboxylic acids, the hydroxycarboxylic acid esters, and also the mixtures of hydroxycarboxylic acids and esters thereof, and also polymeric hydroxycarboxylic acids and esters thereof may also be very particularly preferred. Preferred hydroxycarboxylic acid esters are, for example, full esters of glycolic acid, lactic acid, malic acid, tartaric acid or citric acid. Further fundamentally suitable hydroxycarboxylic acid esters are esters of β-hydroxypropionic acid, of tartronic acid, of D-gluconic acid, of sugar acid, of mucic acid or of glucuronic acid. Suitable as alcohol component of these esters are primary, linear or branched aliphatic alcohols having 8-22 carbon atoms, thus, for example, fatty alcohols or synthetic fatty alcohols. Here, the esters of $C_{12}$-$C_{15}$-fatty alcohols are particularly preferred. Esters of this type are commercially available, e.g. under the trade name Cosmacol® from EniChem, Augusta Industriale. Particularly preferred polyhydroxypolycarboxylic acids are polylactic acid and polytartaric acid, and esters thereof.

Within the scope of a seventh preferred embodiment, the color-modifying agents according to the invention comprise at least one protein hydrolyzate and one of its derivatives as care substance.

Protein hydrolyzates are product mixtures which are obtained by acid-, base- or enzyme-catalyzed degradation of proteins. According to the invention, the term protein hydrolyzates is also understood as meaning total hydrolyzates as well as individual amino acids and derivatives thereof, and mixtures of different amino acids. In addition, according to the invention, polymers constructed from amino acids and amino acid derivatives are understood by the term protein hydrolyzates. The latter include, for example, polyalanine, polyasparagine, polyserine etc. Further examples of compounds which can be used according to the invention are L-alanyl-L-proline, polyglycine, glycyl-L-glutamine or D/L-methionine-5-methylsulfonium chloride. Of course, β-amino acids and derivatives thereof, such as β-alanine, anthranilic acid or hippuric acid, can also be used according to the invention. The molecular weight of the protein hydrolyzates which can be used according to the invention is between 75, the molecular weight of glycine, and 200 000, preferably the molecular weight is 75 to 50 000 and very particularly preferably 75 to 20 000 daltons.

According to the invention, protein hydrolyzates either of vegetable or animal or marine or synthetic origin can be used.

Animal protein hydrolyzates are, for example, elastin, collagen, keratin, silk and milk protein hydrolyzates, which may also be in the form of salts. Such products are sold, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

According to the invention, preference is given to the use of protein hydrolyzates of vegetable origin, e.g. soya, almond, pea, potato and wheat protein hydrolyzates. Such products are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although the use of the protein hydrolyzates as such is preferred, instead of them, it is in some cases also possible to use amino acid mixtures obtained in another way. The use of derivatives of the protein hydrolyzates, for example in the form of their fatty acid condensation products, is likewise possible. Such products are sold, for example, under the names Lamepon® (Cognis), Lexein® (Inolex), Crolastin® (Croda), Crosilk® (Croda) or Crotein® (Croda).

The teaching according to the invention of course includes all isomeric forms, such as cis-, trans-isomers, diastereomers and chiral isomers.

According to the invention, it is also possible to use a mixture of two or more protein hydrolyzates.

The protein hydrolyzates are present in the color-modifying agents according to the invention in concentrations of from 0.01% by weight to 20% by weight, preferably from 0.05% by weight up to 15% by weight and very particularly preferably in amounts of from 0.05% by weight to 5% by weight, in each case based on the total application preparation.

Within the scope of an eighth preferred embodiment, the preparations according to the invention comprise, as care substance, ectoin or ectoin derivatives, allantoin, taurine and bisabolol.

According to the invention, the term "ectoin and ectoin derivatives" is understood as meaning compounds of the formula (IV)

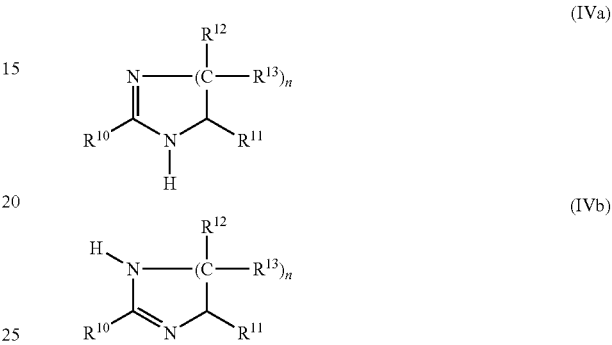

and/or their physiologically compatible salt and/or an isomeric or stereoisomeric form, where $R^{10}$ is a hydrogen atom, a branched or unbranched $C_1$-$C_4$-alkyl radical or a $C_2$-$C_4$-hydroxyalkyl radical, $R^{11}$ is a hydrogen atom, a group —COOR$^{14}$ or a group —CO(NH)R$^{14}$, where R$^{14}$ may be a hydrogen atom, a $C_1$-$C_4$-alkyl radical, an amino acid radical, a dipeptide radical or a tripeptide radical, $R^{12}$ and $R^{13}$, independently of one another, are a hydrogen atom, a $C_1$-$C_4$-alkyl radical or one of the two radicals is a hydroxy group and n is an integer from 1 to 3.

Suitable physiologically compatible salts of the general compounds according to the formula (IVa) or (IVb) are, for example, the alkali metal, alkaline earth metal, ammonium, triethylamine or tris(2-hydroxyethyl)amine salts, and also those which arise from the reaction of compounds according to the formula (IVa) or (IVb) with inorganic and organic acids, such as hydrochloric acid, phosphoric acid, sulfuric acid, branched or unbranched, substituted or unsubstituted (for example by one or more hydroxy groups) $C_1$-$C_4$-mono- or dicarboxylic acids, aromatic carboxylic acids and sulfonic acids, such as acetic acid, citric acid, benzoic acid, maleic acid, fumaric acid, tartaric acid and p-toluenesulfonic acid. Examples of particularly preferred physiologically compatible salts are the Na, K, Mg and Ca and ammonium salts of the compounds according to the formula (IVa) or (IVb), and the salts which arise by reacting compounds according to the formula (IVa) or (IVb) with hydrochloric acid, acetic acid, citric acid and benzoic acid.

According to the invention, isomeric or stereoisomeric forms of the compounds according to formula (IVa) or (IVb) are understood as meaning all optical isomers, diastereomers, racemates, zwitterions, cations or mixtures thereof which arise.

The term amino acid is understood as meaning the stereoisomeric forms, e.g. D and L forms, of the following compounds:

asparagine, arginine, aspartic acid, glutamine, glutamic acid, β-alanine, γ-aminobutyrate, $N_\epsilon$-acetyllysine, $N_\delta$-acetylornithine, $N_\gamma$-acetyldiaminobutyrate, $N_\alpha$-acetyldiaminobutyrate, histidine, isoleucine, leucine, methionine, phenylalanine, serine, threonine and tyrosine. L-amino acids are preferred. Amino acid radicals are derived from the corresponding amino acids. The following amino acid radicals are preferred:

Gyl, Ala, Ser, Thr, Val, β-Ala, γ-aminobutyrate, Asp, Glu, Asn, Aln, $N_\epsilon$-acetyllysine, $N_\epsilon$-acetylornithine, $N_\gamma$-acetyldiaminobutyrate, $N_\alpha$-acetyldiaminobutyrate.

The shorthand of the amino acids was in accordance with the generally customary style. The di- or tripeptide radicals are like acid amides in their chemical nature and decompose upon hydrolysis into 2 or 3 amino acids. The amino acids in the di- or tripeptide radical are joined together by amide bonds.

With regard to the preparation of the di- and tripeptide radicals, reference is made expressly to EP 0 671 161 A1 from Marbert. Examples of di- and tripeptide radicals are also found in the disclosure of EP 0 671 161 A1.

Examples of $C_1$-$C_4$-alkyl groups in the compounds according to the invention are methyl, ethyl, n-propyl, isopropyl, n-butyl, isobutyl and tert-butyl. Preferred alkyl groups are methyl and ethyl, methyl is a particularly preferred alkyl group. Preferred $C_2$-$C_4$-hydroxyalkyl groups are the groups 2-hydroxyethyl, 3-hydroxypropyl or 4-hydroxybutyl; 2-hydroxyethyl is a particularly preferred hydroxyalkyl group.

The color-modifying agents according to the invention comprise these active ingredients preferably in amounts of from 0.001 to 2% by weight, in particular from 0.01 to 0.5% by weight, in each case based on the total application preparation.

Within the scope of a ninth preferred embodiment, the color-modifying agents according to the invention comprise at least one mono- or oligosaccharide as care substance.

It is possible to use either monosaccharides or oligosaccharides, such as, for example, cane sugar, lactose and raffinose. The use of monosaccharides is preferred according to the invention. Of the monosaccharides, preference is in turn given to those compounds which contain 5 or 6 carbon atoms.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are preferably used carbohydrates; very particular preference is given to using glucose, which is suitable both in the D-(+)- or L-(−)-configuration or as racemate.

Furthermore, derivatives of these pentoses and hexoses, such as the corresponding aldonic and uronic acids (sugar acids), sugar alcohols and glycosides, can also be used according to the invention. Preferred sugar acids are gluconic acid, glucuronic acid, saccharic acid, mannosaccharic acid and mucic acid. Preferred sugar alcohols are sorbitol, mannitol and dulcitol. Preferred glycosides are the methyl glycosides.

Since the mono- and oligosaccharides used are usually obtained from natural raw materials such as starch, they usually have the configurations corresponding to these raw materials (e.g. D-glucose, D-fructose and D-galactose).

The mono- and oligosaccharides are present in the hair-treatment agents according to the invention preferably in an amount of from 0.1 to 8% by weight, in particular 1 to 5% by weight, based on the total application preparation.

Within the scope of a tenth embodiment, the preparation according to the invention comprises at least one silicone oil and/or one silicone gum as care substance.

Silicones or silicone gums suitable according to the invention are, in particular, dialkyl- and alkylarylsiloxanes, such as, for example, dimethylpolysiloxane and methylphenylpolysiloxane, and their alkoxylated, quaternized or anionic derivatives.

Examples of such silicones are:
oligomeric polydimethylcyclosiloxanes (INCI name: Cyclomethicone), in particular the tetrameric and the pentameric compound, which are sold as commercial products DC 344 and DC 345 by Dow Corning, hexamethyldisiloxane (INCI name: Hexamethyldisiloxane), e.g. the product sold under the name Abil® K 520, polymeric polydimethylsiloxanes (INCI name: Dimethicone), e.g. the products sold under the name DC 200 by Dow Corning, polyphenylmethylsiloxanes (INCI name: Phenyl Trimethicone), e.g. the commercial product DC 556 Fluid from Dow Corning, silicone-glycol copolymers (INCI name: Dimethicone Copolyol), e.g. the commercial products DC 190 and DC 193 from Dow Corning, esters and partial esters of the silicone-glycol copolymers, as are sold, for example, by Fanning under the trade name Fancorsil® LIM (INCI name: Dimethicone Copolyol Meadowfoamate), dimethylsiloxanes with hydroxy end groups (INCI name: Dimethiconol), e.g. the commercial products DC 1401 and Q2-1403 from Dow Corning, aminofunctional polydimethylsiloxanes and hydroxy-lamino-modified silicones (INCI name: inter alia Amodimethicone and Quaternium-80), such as the commercial products XF42-B1989 (manufacturer GE Toshiba Silicones) □2-7224 (manufacturer: Dow Corning; a stabilized trimethylsilylamodimethicone), Dow Corning® 939 emulsion (comprising a hydroxylamino-modified silicone, which is also referred to amodimethicone), SM-2059 (manufacturer: General Electric), SLM-55067 (manufacturer: Wacker), and Abil®-Quat 3270 and 3272 (manufacturer: Th. Goldschmidt), anionic silicone oils, such as, for example, the product Dow Corning® 1784 amino-modified organosilicones, such as, for example, the product Abil Soft A843 (manufacturer Osi Specialities).

According to a preferred embodiment, the preparations according to the invention comprise a combination of a volatile silicone and a nonvolatile silicone. For the purposes of the invention, volatile silicones are those which have a volatility which is greater than or equal to the volatility of the cyclic pentameric dimethylsiloxane. Such combinations are also available as commercial products (e.g. Dow Corning® 1401, Dow Corning® 1403 and Dow Corning® 1501, in each case mixtures of a cyclomethicone and a dimethiconol).

According to a particularly preferred embodiment, a dialkylpolysiloxane or one of its derivatives is used as component (A). Preference is given to the alkyl groups methyl, ethyl, isopropyl and n-propyl. Dimethylpolysiloxane or one of its derivatives is particularly preferably used. Preference is given to the derivatives of dimethylpolysiloxane which are amino-functional. A very particularly preferred derivative is commercially available under the INCI name Amodimethicone.

The preparations according to the invention comprise the silicones preferably in amounts of 0.01-10% by weight, in particular 0.1-5% by weight, based on the total application preparation.

Within the scope of an eleventh embodiment, the color-modifying agents according to the invention comprise at least one lipid as care substance.

Lipids suitable according to the invention are phospholipids, for example soya lecithin, egg lecithin and cephalins, and the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are sold, for example, by Mona under the tradenames Phospholipid EFA®, Phospholipid PTC® and Phospholipid SV®.

The preparations according to the invention comprise the lipids preferably in amounts of 0.01-10% by weight, in particular 0.1-5% by weight, based on the total application preparation.

Within the scope of a twelfth embodiment, the color-modifying agents according to the invention comprise at least one oil substance as care substance.

The natural and synthetic cosmetic oil substances include, for example:

Vegetable oils. Examples of such oils are sunflower oil, olive oil, soya oil, rapeseed oil, almond oil, jojoba oil, orange oil, wheat germ oil, peach kernel oil and the liquid fractions of coconut oil. Also suitable, however, are other triglyceride oils, such as the liquid fractions of beef tallow, and synthetic triglyceride oils.

Liquid paraffin oils, isoparaffin oils and synthetic hydrocarbons, and di-n-alkyl ethers with a total of between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, and di-tert-butyl ether, diisopentyl ether, di-3-ethyldecyl ether, tert-butyl n-octyl ether, isopentyl n-octyl ether and 2-methylpentyl n-octyl ether. The compounds 1,3-di(2-ethylhexyl)cyclohexane (Cetiol® S) and di-n-octyl ether (Cetiol® OE), which are available as commercial products, may be preferred.

Ester oils. Ester oils are understood as meaning the esters of $C_6$-$C_{30}$-fatty acids with $C_2$-$C_{30}$-fatty alcohols. Preference is given to the monoesters of the fatty acids with alcohols having 2 to 24 carbon atoms. Examples of fatty acid moieties used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof, which are produced, for example, during the pressurized cleavage of natural fats and oils, during the oxidation of aldehydes from the Roelen oxo synthesis or the dimerization of unsaturated fatty acids. Examples of the fatty alcohol moieties in the ester oils are isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachidyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxo synthesis, and as monomer fraction during the dimerization of unsaturated fatty alcohols. According to the invention, particular preference is given to isopropyl myristate (Rilanit® IPM), isononanoic acid C16-18-alkyl ester (Cetiol® SN), 2-ethylhexyl palmitate (Cegesoft® 24), 2-ethylhexyl stearate (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoate (Cetiol® SN), decyl oleate (Cetiol® V).

Dicarboxylic acid esters, such as di-n-butyl adipate, di(2-ethylhexyl) adipate, di(2-ethylhexyl) succinate and diisotridecyl acelate, and diol esters, such as ethylene glycol dioleate, ethylene glycol diisotridecanoate, propylene glycol di(2-ethylhexanoate), propylene glycol diisostearate, propylene glycol dipelargonate, butanediol diisostearate, neopentyl glycol dicaprylate, Symmetrical, asymmetrical or cyclic esters of carbonic acid with fatty alcohols, for example described in DE-A 197 56 454, glycerol carbonate or dicaprylyl carbonate (Cetiol® CC), Trifatty acid esters of saturated and/or unsaturated linear and/or branched fatty acids with glycerol, Fatty acid partial glycerides, i.e. monoglycerides, diglycerides and technical-grade mixtures thereof. When using technical-grade products, small amounts of triglycerides may also be present as a result of the preparation. The partial glycerides preferably conform to the formula (D4-I),

in which $R^1$, $R^2$ and $R^3$, independently of one another, are hydrogen or a linear or branched, saturated and/or unsaturated acyl radical having 6 to 22, preferably 12 to 18, carbon atoms, with the proviso that at least one of these groups is an acyl radical and at least one of these groups is hydrogen. The sum (m+n+q) is 0 or numbers from 1 to 100, preferably 0 or 5 to 25. Preferably, $R^1$ is an acyl radical and $R^2$ and $R^3$ are hydrogen and the sum (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof. Oleic acid monoglycerides are preferably used.

The use amount of the natural and synthetic cosmetic oil substances in the color-modifying agents according to the invention is usually 0.1-30% by weight, based on the total application preparation, preferably 0.1-20% by weight, and in particular 0.1-15% by weight.

Within the scope of a thirteenth embodiment, the preparations according to the invention comprise an enzyme as care substance. Enzymes particularly preferred according to the invention are chosen from a group which is formed from proteases, lipases, transglutaminase, oxidases and peroxidases.

Although each of the care substances given in the various embodiments produces a satisfactory result by itself, the scope of the present invention also extends to all embodiments in which the color-modifying agents comprise a plurality of care substances, possibly from different groups.

Besides the components essential for the invention, the color-modifying agents according to the invention can also comprise all active ingredients, additives and auxiliaries known for such preparations.

In many cases, the color-modifying agents comprise at least one surfactant, where in principle either anionic or zwitterionic, ampholytic, nonionic and cationic surfactants are suitable. However, in many cases, it has proven to be advantageous to choose the surfactants from anionic, zwitterionic or nonionic surfactants. As regards the cationic surfactants, reference may be made at this point to the statements above.

Suitable anionic surfactants in preparations according to the invention are all anionic surface-active substances suitable for use on the human body. These are characterized by a water-solubilizing, anionic group, such as, for example, a carboxylate, sulfate, sulfonate or phosphate group, and a lipophilic alkyl group having about 10 to 22 carbon atoms. In addition, glycol or polyglycol ether groups, ester, ether and amide groups, and hydroxyl groups may be present in the molecule. Examples of suitable anionic surfactants are, in each case in the form of the sodium, potassium and ammonium salts, and also the mono-, di- and trialkanolammonium salts having 2 or 3 carbon atoms in the alkanol group, linear fatty acids having 10 to 22 carbon atoms (soaps),
ether carboxylic acids of the formula R—O—($CH_2$—$CH_2O$)$_x$—$CH_2$—COOH, in which R is a linear alkyl group having 10 to 22 carbon atoms and x=0 or 1 to 16,
acyl sarcosides having 10 to 18 carbon atoms in the acyl group,
acyl taurides having 10 to 18 carbon atoms in the acyl group,
acyl isethionates having 10 to 18 carbon atoms in the acyl group,
sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
linear alkanesulfonates having 12 to 18 carbon atoms,
linear alpha-olefinsulfonates having 12 to 18 carbon atoms,
alpha-sulfo fatty acid methyl esters of fatty acids having 12 to 18 carbon atoms,
alkyl sulfates and alkyl polyglycol ether sulfates of the formula R—O($CH_2$—$CH_2O$)$_x$—$SO_3$H, in which R is a preferably linear alkyl group having 10 to 18 carbon atoms and x=0 or 1 to 12,
mixtures of surface-active hydroxysulfonates according to DE-A-37 25 030,
sulfated hydroxyalkylpolyethylene and/or hydroxyalkylenepropylene glycol ethers as in DE-A-37 23 354,
sulfonates of unsaturated fatty acids having 12 to 24 carbon atoms and 1 to 6 double bonds as in DE-A-39 26 344,
esters of tartaric acid and citric acid with alcohols, which constitute addition products of about 2-15 molecules of ethylene oxide and/or propylene oxide onto fatty alcohols having 8 to 22 carbon atoms.

Preferred anionic surfactants are alkyl sulfates, alkyl polyglycol ether sulfates and ether carboxylic acids having 10 to 18 carbon atoms in the alkyl group and up to 12 glycol ether groups in the molecule, and in particular salts of saturated and in particular unsaturated $C_8$-$C_{22}$-carboxylic acids, such as oleic acid, stearic acid, isostearic acid and palmitic acid.

Nonionogenic surfactants comprise, as hydrophilic group, e.g. a polyol group, a polyalkylene glycol ether group or a combination of polyol and polyglycol ether group. Such compounds are, for example, addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
$C_{12}$-$C_{22}$ fatty acid mono- and diesters of addition products of from 1 to 30 mol of ethylene oxide onto glycerol,
$C_8$-$C_{22}$-alkyl mono- and oligoglycosides and ethoxylated analogs thereof, and
addition products of from 5 to 60 mol of ethylene oxide onto castor oil and hydrogenated castor oil.

Preferred nonionic surfactants are alkyl polyglycosides of the general formula $R^1$O-$(Z)_x$. These compounds are characterized by the following parameters.

The alkyl radical $R^1$ comprises 6 to 22 carbon atoms and may either be linear or branched. Preference is given to primary aliphatic radicals which are linear or methyl-branched in the 2 position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. When using so-called "oxo alcohols" as starting materials, compounds with an uneven number of carbon atoms in the alkyl chain predominate.

The alkyl polyglycosides which can be used according to the invention can, for example, comprise only one particular alkyl radical $R^1$. Usually, however, these compounds are prepared starting from natural fats and oils or mineral oils. In this case, the alkyl radicals R present are mixtures corresponding to the starting compounds and/or corresponding to the particular work-up of these compounds.

Particular preference is given to those alkyl polyglycosides in which $R^1$ consists
essentially of $C_8$- and $C_{10}$-alkyl groups,
essentially of $C_{12}$- and $C_{14}$-alkyl groups,
essentially of $C_8$- to $C_{16}$-alkyl groups or
essentially of $C_{12}$- to $C_{16}$-alkyl groups.

Sugar building blocks Z which may be used are any mono- or oligosaccharides. Usually, sugars with 5 or 6 carbon atoms and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention comprise, on average, 1.1 to 5 sugar units. Alkyl polyglycosides with x values of from 1.1 to 1.6 are preferred. Very particular preference is given to alkyl glycosides in which x is 1.1 to 1.4.

Besides their surfactant effect, the alkyl glycosides can also serve to improve the fixing of scent components on the hair. Thus, if an effect of the perfume oil on the hair which lasts beyond the duration of the hair treatment is desired, the person skilled in the art will preferably have recourse to this class of substance as further ingredient of the preparations according to the invention.

The alkoxylated homologs of the specified alkyl polyglycosides can also be used according to the invention. These homologs can on average comprise up to 10 ethylene oxide and/or propylene oxide units per alkyl glycoside unit.

In addition, zwitterionic surfactants can be used, especially as cosurfactants. Zwitterionic surfactants is the term used to refer to those surface-active compounds which carry at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethylglycinate. A preferred zwitterionic surfactant is the fatty acid amide derivative known under the INCI name Cocamidopropyl Betaine.

Likewise particularly suitable as cosurfactants are ampholytic surfactants. Ampholytic surfactants are understood as meaning those surface-active compounds which, apart from a C$_8$-C$_{18}$-alkyl or acyl group, comprise at least one free amino group and at least one —COOH or —SO$_3$H group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and C$_{12-18}$-acylsarcosine.

The compounds with alkyl groups used as surfactant may each be individual substances. However, it is usually preferred to start from natural vegetable or animal raw materials when preparing these substances, resulting in mixtures of substances with varying alkyl chain lengths which depend on the particular raw material.

The surfactants which constitute addition products of ethylene oxide and/or propylene oxide onto fatty alcohols or derivatives of these addition products and may be used are either products with a "normal" homolog distribution, or those with a narrowed homolog distribution. "Normal" homolog distribution is understood here as meaning mixtures of homologs which are obtained when reacting fatty alcohol and alkylene oxide using alkali metals, alkali metal hydroxides or alkali metal alkoxides as catalysts. Narrowed homolog distributions, by contrast, are obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

In addition, the color-modifying agents according to the invention can comprise further active ingredients, auxiliaries and additives, such as, for example,

- nonionic polymers, such as, for example, vinylpyrrolidone/vinyl acrylate copolymers, polyvinylpyrrolidone and vinylpyrrolidone/vinyl acetate copolymers and polysiloxanes,
- zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers,
- thickeners, such as agar-agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids such as, for example, polyvinyl alcohol,
- structurants, such as maleic acid and lactic acid,
- hair conditioning compounds, such as phospholipids, for example soya lecithin, egg lecithin and cephalins,
- protein hydrolyzates, in particular elastin, collagen, keratin, milk protein, soya protein and wheat protein hydrolyzates, condensation products thereof with fatty acids, and quaternized protein hydrolyzates,
- perfume oils, dimethyl isosorbide and cyclodextrins,
- solvents and solubilizers such as ethanol, ispropanol, ethylene glycol, propylene glycol, glycerol and diethylene glycol,
- active ingredients which improve the fiber structure, in particular mono-, di- and oligosaccharides, such as, for example, glucose, galactose, fructose, fruit sugar and lactose,
- quaternized amines, such as methyl-1-alkylamidoethyl-2-alkylimidazolium methosulfate,
- antifoams, such as silicones,
- dyes for coloring the agent,
- antidandruff active ingredients, such as piroctone olamine, zinc omadine and climbazole,
- photoprotective agents, in particular derivatized benzophenones, cinnamic acid derivatives and triazines,
- substances for adjusting the pH, such as, for example, customary acids, in particular food acids and bases,
- active ingredients, such as allantoin, pyrrolidonecarboxylic acids and salts thereof, and bisabolol,
- cholesterol,
- consistency regulators such as sugar esters, polyol esters or polyol alkyl ethers,
- fats and waxes, such as spermaceti, beeswax, montan wax and paraffins,
- fatty acid alkanolamides,
- complexing agents, such as EDTA, NTA, β-alaninediacetic acid and phosphonic acids,
- swelling and penetration substances, such as glycerol, propylene glycol monoethyl ether, carbonates, hydrogencarbonates, guanidines, ureas, and primary, secondary and tertiary phosphates,
- opacifiers, such as latex, styrene/PVP and styrene/acrylamide copolymers,
- pearlizing agents, such as ethylene glycol mono- and distearate, and PEG-3 distearate,
- preservatives,
- stabilizers for hydrogen peroxide and other oxidizing agents,
- propellants, such as propane-butane mixtures, N$_2$O, dimethyl ether, CO$_2$ and air,
- antioxidants.

With regard to further optional components and the amounts used of these components, reference is made expressly to the relevant handbooks known to the person skilled in the art, e.g. Kh. Schrader, Grundlagen und Rezepturen der Kosmetika [Fundamentals and formulations of cosmetics], 2nd edition, Hüthig Buch Verlag, Heidelberg, 1989.

According to the invention, the color-modifying agents comprise the components essential for the invention preferably in a suitable aqueous, alcoholic or aqueous-alcoholic carrier. For the purpose of coloring hair, such carriers are, for example, creams, emulsions, gels or surfactant-containing foaming solutions, such as, for example, shampoos, foam aerosols or other preparations which are suitable for use on the hair.

For the purposes of the present invention, aqueous-alcoholic solutions are understood as meaning aqueous solutions comprising 3 to 70% by weight of a $C_1$-$C_4$-alcohol, in particular ethanol or isopropanol. The agents according to the invention can additionally comprise further organic solvents, such as, for example, methoxybutanol, benzyl alcohol, ethyl diglycol or 1,2-propylene glycol. Preference is given here to all water-soluble organic solvents.

In addition, the color-modifying agents according to the invention can comprise a reducing agent. Examples of reducing agents preferred according to the invention are sodium sulfite, ascorbic acid, thioglycolic acid and derivatives thereof, sodium thionite, alkali metal citrate salts and N-acetyl-L-cysteine. Very particularly preferred reducing agents are alkali metal citrate salts, in particular sodium citrate, and N-acetyl-L-cysteine. N-Acetyl-L-cysteine is a very particularly preferred reducing agent.

Furthermore, the agents according to the invention can comprise alkalinizing agents, usually alkali metal or alkaline earth metal hydroxides, ammonia or organic amines. Preferred alkalinizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine, and also alkali metal and alkaline earth metal hydroxides. Especially monoethanolamine, triethanolamine and 2-amino-2-methylpropanol and 2-amino-2-methyl-1,3-propanediol are preferred within this group. The use of ω-amino acids, such as (ω-aminocaproic acid, as alkalinizing agent is also possible.

Pearlescent pigments are often used for this purpose. Pearlescent pigments preferred according to the invention are natural pearlescent pigments, such as, for example, pearl essence (guanine/hypoxanthine mixed crystals from fish scales) or mother of pearl (from ground mussel shells), monocrystalline pearlescent pigments, such as, for example, bismuth oxychloride, and pearlescent pigments based on mica or mica/metal oxide. The last-mentioned pearlescent pigments are provided with a metal oxide coating. Use of the pearlescent pigments achieves shine and, if appropriate, additionally color effects in the compositions according to the invention. However, the imparting of color through the pearlescent pigments used in the compositions does not influence the color result of the coloration of the keratin fibers.

Pearlescent pigments based on mica and on mica/metal oxide are likewise preferred according to the invention. Mica is a type of sheet silicate. The most important representatives of these silicates are muscovite, phlogopite, paragonite, biotite, lepidolite and margarite. To produce the pearlescent pigments in combination with metal oxides, the mica, predominantly muscovite or phlogopite, is coated with a metal oxide. Suitable metal oxides are, inter alia, $TiO_2$, $Cr_2O_3$ and $Fe_2O_3$. Appropriate coating produces interference pigments, and colored luster pigments as pearlescent pigments according to the invention. Besides having a glittering optical effect, these types of pearlescent pigment additionally have color effects. Furthermore, the pearlescent pigments which can be used according to the invention can also comprise a colored pigment that is not derived from a metal oxide.

The particle size of the preferably used pearlescent pigments is preferably between 1.0 and 100 µm, particularly preferably between 5.0 and 60.0 µm.

Particularly preferred pearlescent pigments are pigments which are marketed by Merck under the trade names Colorona®, where the pigments Colorona® red-brown (47-57% by weight of muscovite mica ($KH_2(AlSiO_4)_3$), 43-50% by weight of $Fe_2O_3$ (INCI: Iron Oxides CI 77491), <3% by weight of $TiO_2$ (INCI: Titanium Dioxide CI 77891), Colorona® Blackstar Blue (39-47% by weight of muscovite mica ($KH_2(AlSiO_4)_3$), 53-61% by weight of $Fe_3O_4$ (INCI: Iron Oxides CI 77499)), Colorona® Siena Fine (35-45% by weight of muscovite mica ($KH_2(AlSiO_4)_3$), 55-65% by weight of $Fe_2O_3$ (INCI: Iron Oxides CI 77491)), Colorona® Aborigine Amber (50-62% by weight of muscovite mica ($KH_2(AlSiO_4)_3$), 36-44% by weight of $Fe_3O_5$ (INCI: Iron Oxides CI 77499), 2-6% by weight of $TiO_2$ (INCI: Titanium Dioxide CI 77891)), Colorona® Patagonium Purple (42-54% by weight of muscovite mica ($KH_2(AlSiO_4)_3$), 26-32% by weight of $Fe_2O_3$ (INCI: Iron Oxides CI 77491), 18-22% by weight of $TiO_2$ (INCI: Titanium Dioxide CI 77891), 2-4% by weight of Prussian Blue (INCI: Ferric Ferrocyanide CI 77510)), Colorona® Chameleon (40-50% by weight of muscovite mica ($KH_2(AlSiO_4)_3$), 50-60% by weight of $Fe_2O_3$ (INCI: Iron Oxides CI 77491)) and Silk® Mica (>98% by weight of muscovite mica ($KH_2(AlSiO_4)_3$).

With regard to the pearlescent pigments which can be used in the compositions according to the invention, reference is also expressly made to the monographs Inorganic Pigments, Chemical Technology Review No. 166, 1980, pages 161-173 (ISBN 0-8155-0811-5) and Industrial Inorganic Pigments, 2nd edition, Weinheim, VCH, 1998, pages 211-231.

If the formation of the actual coloration takes place in the course of an oxidative process, then customary oxidizing agents, such as, in particular, hydrogen peroxide or its addition products onto urea, melamine or sodium borate can be used. Oxidation with atmospheric oxygen as the sole oxidizing agent may, however, be preferred. However, preference is given to using a chemical oxidizing agent, particularly when, besides the coloring, a lightening effect on human hair is desired. Suitable oxidizing agents are persulfates, chlorites and in particular hydrogen peroxide or its addition products onto urea, melamine, and sodium borate. According to the invention, however, the oxidation colorant can also be applied to the hair together with a catalyst which activates the oxidation of the dye precursors, e.g. by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particular suitability here are $Zn^{2+}$, $Cu^{2+}$ and $Mn^{2+}$. The metal ions can in principle be used in the form of any physiologically compatible salt or in the form of a complex compound. Preferred salts are the acetates, sulfates, halides, lactates and tartrates. Through using these metal salts, it is possible to both accelerate the formation of the coloration, and also to influence the color nuance in a targeted manner.

Suitable enzymes are, for example, peroxidases, which can significantly increase the effect of small amounts of hydrogen peroxide. Also suitable according to the invention are those enzymes which directly oxidize the oxidation dye precursors with the help of atmospheric oxygen, such as, for example, the laccases, or produce in situ small amounts of hydrogen peroxide and in so doing biocatalytically activate the oxidation of the dye precursors. Particularly suitable catalysts for the oxidation of the dye precursors are the so-called 2-electron oxidoreductases in combination with the substrates specific for this purpose, e.g.

pyranose-oxidase and e.g. D-glucose or galactose,
    glucose-oxidase and D-glucose,
    glycerol-oxidase and glycerol,
    pyruvate-oxidase and pyruvic acid or salts thereof,
    alcohol-oxidase and alcohol (MeOH, EtOH),
    lactate-oxidase and lactic acid and salts thereof,
    tyrosinase-oxidase and tyrosine,
    uricase and uric acid or salts thereof,
    choline oxidase and choline,
    amino acid-oxidase and amino acids.

The actual oxidative colorant is expediently prepared directly prior to application by mixing the preparation of the oxidizing agent with the preparation comprising the dye precursors. The resulting ready-to-use hair-dyeing preparation should preferably have a pH in the range from 5 to 14, in particular from 7 to 12. Particular preference is given to using the hair colorants in a weakly alkaline medium. The application temperatures can be in a range between 15 and 40° C. After a contact time of 5 to 45 minutes, the hair colorant is removed from the hair to be dyed by rinsing. After-washing with a shampoo is dispensed with if a carrier with a high content of surfactant, e.g. a color shampoo, has been used.

Particularly in the case of hair which is difficult to dye, the preparation containing the dye precursors can, however, also be applied to the hair without prior mixing with the oxidation component. After a contact time of 20 to 30 minutes, the oxidation component is then applied—optionally after intermediate rinsing. After a further contact time of 10 to 20 minutes, the hair is then rinsed and, if desired, after-shampooed. In the case of this embodiment, according to a first variant in which the prior application of the dye precursors should bring about better penetration into the hair, the corresponding composition is adjusted to a pH of about 4 to 7. According to a second variant, an air oxidation is firstly desired, in which case the applied composition preferably has a pH of from 7 to 10. During the subsequent accelerated post-oxidation, the use of peroxydisulfate solutions which have been rendered acidic as oxidizing agent may be preferred.

The present invention secondly provides a method of coloring keratin fibers in which one of the agents according to the invention is optionally mixed with an oxidizing agent preparation, the application preparation is applied to the fibers and, after a contact time, is rinsed out again.

The present invention thirdly provides the use of at least one protein of the seed of the genus of the *moringa* plants for increasing the care effect of color-modifying agents for keratin fibers.

The present invention fourthly provides the use of at least one protein of the seed of the genus of the *moringa* plants in colorants for keratin fibers based on direct dyes and/or dye precursors to protect the fibers against UV radiation.

WORKING EXAMPLES

Unless stated otherwise, the data below is in percent by weight.

The coloring creams from 1 to XVI (tables 1-4) described below were prepared and in each case mixed in the ratio 1:1 with the following oxidizing agent preparation directly prior to use:

| Raw material | Amount |
| --- | --- |
| Dipicolinic acid | 0.1 |
| 50% strength KOH | 0.3 |
| Sodium benzoate | 0.04 |
| Sodium pyrophosphate | 0.1 |
| Turpinal ® SL | 0.4 |
| 1,2-Propylene glycol | 0.4 |
| Cetyl/stearyl alcohol 50:50 | 4.0 |
| Dehyquart ® B | 0.75 |
| Emulgin ® B2 | 1.2 |
| Paraffin oil | 0.3 |
| 50% strength $H_2O_2$ | 12.2 |
| Water | ad 100.0 |

The resulting application mixture was applied to tresses of buffalo stomach hair and left there for 30 minutes at room temperature. The fibers were then thoroughly rinsed with water and the colorations were ascertained.

TABLE 1

| Raw material | Coloring cream I | Coloring cream II | Coloring cream III | Coloring cream IV |
| --- | --- | --- | --- | --- |
| Ammonium carbopol solution (1% in water) | 15.0 | 15.0 | 15.0 | 15.0 |
| Lanette ® E | 0.7 | 0.7 | 0.7 | 0.7 |
| Lauryl ether sulfate (27% active substance) | 4.4 | 4.4 | 4.4 | 4.4 |
| PEG 400 | 0.6 | 0.6 | 0.6 | 0.6 |
| Potassium oleate (12.5% active substance) | 3.0 | 3.0 | 3.0 | 3.0 |
| Titanium dioxide | 0.5 | 0.5 | 0.5 | 0.5 |
| Cetylstearyl alcohol 50/50 | 12.0 | 12.0 | 12.0 | 12.0 |
| Eumulgin ® B2 | 3.0 | 3.0 | 3.0 | 3.0 |
| Eutanol ® G | 2.0 | 2.0 | 2.0 | 2.0 |
| Cutina ® AGS | 2.0 | 2.0 | 2.0 | 2.0 |
| Cutina ® GMS-SE | 2.00 | 2.0 | 2.0 | 1.0 |
| Potassium hydroxide solution 50% | 0.9 | 0.9 | 0.9 | 0.9 |
| Tetrasodium EDTA | 0.2 | 0.2 | 0.2 | 0.2 |
| Sodium sulfite | 0.2 | 0.2 | 0.2 | 0.2 |
| Ascorbic acid | 0.05 | 0.05 | 0.05 | 0.05 |
| Merquat Plus ® 3330 | 1.5 | 1.5 | 1.5 | 1.5 |
| Perfume | 0.3 | 0.3 | 0.3 | 0.3 |
| Phospholipid ® EFA | 0.1 | 0.1 | 0.1 | 0.1 |
| Puricare ® LS 9658 | 1.0 | 1.0 | 1.0 | 1.0 |
| Silicic acid | 0.25 | 0.25 | 0.25 | 0.25 |
| p-Aminophenol | 0.02 | 0.2 | — | — |
| p-Phenylenediamine | 1.15 | — | — | — |
| 1-(2-hydroxyethyl)-4,5-diaminopyrazole | — | — | 1.5 | 0.9 |
| p-Tolylenediamine | — | 0.97 | 0.18 | — |
| HC Blue No. 7 | — | — | — | 0.40 |
| Resorcinol | 0.60 | 0.45 | — | — |
| o-Aminophenol | 0.06 | — | — | — |
| m-Aminophenol | 0.15 | 0.09 | 0.04 | — |
| 2,6-Diaminopyridine | 0.01 | — | — | — |
| 5-Amino-2-methylphenol | — | 0.06 | 0.80 | — |
| 1-Naphthol | — | — | — | 0.40 |
| 2-Amino-4-hydroxy-ethylaminoanisole sulfate | — | — | — | 0.13 |
| 2-Nitro-p-phenylenediamine | — | 0.20 | — | — |
| Ammonia solution (25%) | ad pH 10.2 | ad pH 10.4 | ad pH 10.2 | ad pH 10.5 |
| Water | ad 100.0 | ad 100.0 | ad 100.0 | ad 100.0 |
| Nuance | pale brown | copper | red | violet |

TABLE 2

| Raw material | Coloring cream V | Coloring cream VI | Coloring cream VII | Coloring cream VIII |
| --- | --- | --- | --- | --- |
| Ammonium carbopol solution (1% in water) | 18.0 | 18.0 | 18.0 | 18.0 |
| Ammonium Rohagit ® (6% in water) | 15.0 | 15.0 | 15.0 | 15.0 |
| Eumulgin ® KE 2602 | 0.7 | 0.7 | 0.7 | 0.7 |
| Potassium oleate | 4.4 | 4.4 | 4.4 | 4.4 |
| Potassium castorate | 0.6 | 0.6 | 0.6 | 0.6 |
| Plantacare ® 2000 UP | 3.0 | 3.0 | 3.0 | 3.0 |
| Titanium dioxide | 0.5 | 0.5 | 0.5 | 0.5 |
| Lanette ® O | 12.0 | 12.0 | 12.0 | 12.0 |
| Cetiol ® V | 3.0 | 3.0 | 3.0 | 3.0 |
| Cutina ® GMS V | 2.0 | 2.0 | 2.0 | 2.0 |
| Potassium hydroxide solution 50% | 0.9 | 0.9 | 0.9 | 0.9 |
| Tetrasodium EDTA | 0.2 | 0.2 | 0.2 | 0.2 |
| Sodium sulfite | 0.2 | 0.2 | 0.2 | 0.2 |
| Ascorbic acid | 0.05 | 0.05 | 0.05 | 0.05 |

TABLE 2-continued

| Raw material | Coloring cream V | Coloring cream VI | Coloring cream VII | Coloring cream VIII |
|---|---|---|---|---|
| Mirapol ® A 15 | 1.5 | 1.5 | 1.5 | 1.5 |
| Perfume | 0.3 | 0.3 | 0.3 | 0.3 |
| Phospholid ® EFA | 0.1 | 0.1 | 0.1 | 0.1 |
| Puricare ® LS 9658 | 1.0 | 1.0 | 1.0 | 1.0 |
| Silicic acid | 0.25 | 0.25 | 0.25 | 0.25 |
| p-Aminophenol | 0.02 | 0.2 | — | — |
| p-Phenylenediamine | 1.15 | — | — | — |
| 1-(2-Hydroxyethyl)-4,5-diaminopyrazole | — | — | 1.5 | 0.93 |
| p-Tolylenediamine | — | 0.97 | 0.18 | — |
| HC Blue No. 7 | — | — | — | 0.40 |
| Resorcinol | 0.60 | 0.45 | — | — |
| o-Aminophenol | 0.06 | — | — | — |
| m-Aminophenol | 0.15 | 0.09 | 0.04 | — |
| 2,6-Diaminopyridine | 0.011 | — | — | — |
| 5-Amino-2-methylphenol | — | 0.06 | 0.80 | — |
| 1-Naphthol | — | — | — | 0.40 |
| 2-Amino-4-hydroxy-ethylaminoanisole sulfate | — | — | — | 0.13 |
| 2-Nitro-p-phenylenediamine | — | 0.20 | — | — |
| Ammonia solution (25%) | ad 10.2 | ad 10.4 | ad 10.3 | ad 10.5 |
| Water | ad 100.0 | ad 100.0 | ad 100.0 | ad 100.0 |
| Nuance | pale brown | copper | red | violet |

TABLE 3

| Raw material | Coloring cream IX | Coloring cream X | Coloring cream XI | Coloring cream XII |
|---|---|---|---|---|
| Ammonium carbopol solution (1% in water) | 15.0 | 15.0 | 15.0 | 15.0 |
| Lanette ® E | 0.70 | 0.7 | 0.7 | 0.7 |
| Lauryl ether sulfate (27% in water) | 4.4 | 4.4 | 4.4 | 4.4 |
| PEG 600 | 0.6 | 0.6 | 0.6 | 0.6 |
| Potassium oleate (12.5% in water) | 3.0 | 3.0 | 3.0 | 3.0 |
| Titanium dioxide | 0.15 | 0.15 | 0.15 | 0.15 |
| Cetylstearyl alcohol 50/50 | 12.0 | 12.0 | 12.0 | 12.0 |
| Eumulgin ® B2 | 3.0 | 3.0 | 3.0 | 3.0 |
| Eutanol ® G | 2.0 | 2.0 | 2.0 | 2.0 |
| Cutina ® AGS | 2.0 | 2.0 | 2.0 | 2.0 |
| Cutina ® GMS-SE | 2.0 | 2.0 | 2.0 | 2.0 |
| XF42-B1989 ® | 1.5 | 1.5 | 1.5 | 1.5 |
| Glycyrrhiza extracted powder | 0.2 | 0.2 | 0.2 | 0.2 |
| Potassium hydroxide solution 50% | 0.9 | 0.9 | 0.9 | 0.9 |
| Tetrasodium EDTA | 0.4 | 0.4 | 0.4 | 0.4 |
| Sodium sulfite | 0.1 | 0.1 | 0.1 | 0.1 |
| Ascorbic acid | 0.1 | 0.1 | 0.1 | 0.1 |
| Merquat Plus ® 3330 | 1.5 | 1.5 | 1.5 | 1.5 |
| Perfume | 0.5 | 0.5 | 0.5 | 0.5 |
| Puricare ® LS 9658 | 1.0 | 1.0 | 1.0 | 1.0 |
| Silicic acid | 0.25 | 0.25 | 0.25 | 0.25 |
| p-Aminophenol | 0.02 | 0.20 | — | — |
| p-Phenylenediamine | 1.15 | — | — | — |
| 1-(2-Hydroxyethyl)-4,5-diaminopyrazole | — | — | 1.50 | 0.93 |
| p-Tolylenediamine | — | 0.97 | 0.18 | — |
| HC Blue No. 7 | — | — | — | 0.40 |
| Resorcinol | 0.60 | 0.45 | — | — |
| o-Aminophenol | 0.06 | — | — | — |
| m-Aminophenol | 0.15 | 0.09 | 0.04 | — |
| 2,6-Diaminopyridine | 0.01 | — | — | — |
| 5-Amino-2-methylphenol | — | 0.06 | 0.80 | — |
| 1-Naphthol | — | — | — | 0.40 |
| 2-Amino-4-hydroxy-ethylaminoanisole sulf. | — | — | — | 0.13 |
| 2-Nitro-p-phenylenediamine | — | 0.20 | — | — |
| Ammonia solution (25%) | ad 10.2 | ad 10.4 | ad 10.3 | ad 10.5 |
| Water | ad 100.0 | ad 100.0 | ad 100.0 | ad 100.0 |
| Nuance | pale brown | copper | red | violet |

TABLE 4

| Raw material | Coloring cream XIII | Coloring cream XIV | Coloring cream XV | Coloring cream XVI |
|---|---|---|---|---|
| Ammonium carbopol solution (1% in water) | 15.0 | 15.0 | 15.0 | 15.0 |
| Lanette ® E | 0.7 | 0.7 | 0.7 | 0.7 |
| Lauryl ether sulfate (27% in water) | 4.4 | 4.4 | 4.4 | 4.4 |
| PEG 600 | 0.6 | 0.6 | 0.6 | 0.6 |
| Potassium oleate (12.5% in water) | 3.0 | 3.0 | 3.0 | 3.0 |
| Titanium dioxide | 0.15 | 0.15 | 0.15 | 0.15 |
| Cetylstearyl alcohol 50/50 | 12.0 | 12.0 | 12.0 | 12.0 |
| Emulgin ® B2 | 3.0 | 3.0 | 3.0 | 3.0 |
| Eutanol ® G | 2.0 | 2.0 | 2.0 | 2.0 |
| Cutina ® AGS | 2.0 | 2.0 | 2.0 | 2.0 |
| Cutina ® GMS-SE | 2.0 | 2.0 | 2.0 | 2.0 |
| XF42-B1989 ® | 1.5 | 1.5 | 1.5 | 1.5 |
| Glycyrrhiza extracted powder | 0.2 | 0.2 | 0.2 | 0.2 |
| Potassium carbonate, anhydrous | 1.0 | 1.0 | 1.0 | 1.0 |
| Diammonium hydrogenphosphate | 0.6 | 0.6 | 0.6 | 0.6 |
| Tetrasodium EDTA | 0.4 | 0.4 | 0.4 | 0.4 |
| Sodium sulfite | 0.1 | 0.1 | 0.1 | 0.1 |
| Ascorbic acid | 0.1 | 0.1 | 0.1 | 0.1 |
| Merquat Plus ® 3330 | 1.5 | 1.5 | 1.5 | 1.5 |
| Perfume | 0.5 | 0.5 | 0.5 | 0.5 |
| Puricare ® LS 9658 | 1.0 | 1.0 | 1.0 | 1.0 |
| Silicic acid | 0.25 | 0.25 | 0.25 | 0.25 |
| p-Aminophenol | 0.02 | 0.20 | — | — |
| p-Phenylenediamine | 1.15 | — | — | — |
| 1-(2-Hydroxyethyl)-4,5-diaminopyrazole | — | — | 1.50 | 0.93 |
| p-Tolylenediamine | — | 0.97 | 0.18 | — |
| HC Blue No. 7 | — | — | — | 0.40 |
| Resorcinol | 0.60 | 0.45 | — | — |
| o-Aminophenol | 0.06 | — | — | — |
| m-Aminophenol | 0.15 | 0.09 | 0.04 | — |
| 2,6-Diaminopyridine | 0.01 | — | — | — |
| 5-Amino-2-methylphenol | — | 0.06 | 0.80 | — |
| 1-Naphthol | — | — | — | 0.40 |
| 2-Amino-4-hydroxy-ethylaminoanisole sulfate | — | — | — | 0.13 |
| 2-Nitro-p-phenylenediamine | — | 0.20 | — | — |
| Potassium hydroxide solution (50% in water) | ad pH 9.1 | ad pH 9.1 | ad pH 9.1 | ad pH 9.1 |
| Water | ad 100.0 | ad 100.0 | ad 100.0 | ad 100.0 |
| Nuance | pale brown | copper | red | violet |

List of Commercial Products Used

The commercial products used in the course of the examples are defined as follows:

| | |
|---|---|
| Ammonium carbopol solution | Solution of an ammonium salt of a methacrylic acid-methyl acrylate copolymer (INCI name: Ammonium Polyacrylate) (Röhm GmbH) |
| Ammonium rohagit solution | Solution of an ammonium salt of an acrylic acid polymer (INCI name: Ammonium Acrylates Copolymer) (Goodrich) |
| Cetiol ® V | Oleic acid decyl ester (INCI name: Decyl Oleate) (Cognis) |
| Cutina ® AGS | Ethylene glycol distearate (INCI name: Glycol Distearate) (Cognis) |
| Cutina ® GMS-SE | INCI name: Glyceryl Stearate SE (Cognis) |
| Cutina ® GMS-V | Glycerol mono/dipalmitate/stearate (INCI name: Glyceryl Stearate) (Cognis) |
| Dehyquart ® B | Stearyltrimethylammonium chloride (about 60-66% active substance content; INCI name: Steartrimonium Chloride) (Cognis) |
| Eumulgin ® B2 | Cetylstearyl alcohol with about 20 EO units (INCI name: Ceteareth-20) (Cognis) |
| Eumulgin ® KE 2602 | Ethoxylated oleyl alcohol (INCI name: Oleth-7) (Cognis) |
| Eutanol ® G | 2-Octyldodecyl alcohol (INCI name: Octyldodecanol) (Cognis) |
| Glycyrrhiza Extr. Powder | Licorice extract (INCI name: Glycyrrhiza Glabra (Licorice) Root Extract) (Maruzen) |
| HC Blue No. 7 | INCI name: 6-Methoxy-2-methylamino-3-aminopyridine HCl |
| Lanette ® E | Fatty alcohol sulfate sodium salt (about 90-96% active substance content; INCI name: sodium Cetearyl Sulfate) (Cognis) |
| Lanette ® O | $C_{16-18}$-fatty alcohol (INCI name: Cetearyl Alcohol) (Cognis) |
| Merquat ® Plus 3330 | Dimethyldiallylammonium chloride acrylic acid acrylamide terpolymer (about 9.5% solids in water; INCI name: Polyquaternium-39) (Ondeo-Nalco) |
| Mirapol ® A 15 | Poly[N-(3-dimethylammonium)propyl]-N'-[3-ethyleneoxyethylenedimethylammonium)-propyl]urea dichloride (about 64% solids in water; INCI name: Polyquaternium-2) (Rhodia) |
| Phopholipid ® EFA | (about 30% solids in water/propylene glycol: INCI name: Linoleamidopropyl PG-Dimonium Chloride Phosphate) (Uniqema) |
| Plantacare ® 2000 UP | $C_{8-16}$ Alkylglucoside (about 51-55% active substance content in water; INCI name: Decyl Glucoside, Aqua (Water)) (Cognis) |
| Puricare ® LS 9658 | *Moringa Pterygosperma* extract in water/glycerol (about 1% strength solution; INCI name: Water, Glycerine, *Moringa Pterygosperma* Seed Extract) (Cognis) |
| Turpinal ® SL | 1-Hydroxyethane-1,1-diphosphonic acid (about 58-61% active substance content; INCI name: Etidronic Acid, Aqua (Water)) (Solutia) |
| XF42-B1989 ® | Amino-functional silicone (INCI name: Amodimethicone) (GE Bayer Silicones) |

What is claimed is:

1. A composition comprising: (a) a protein from a seed of a plant of the *Moringa* genus; (b) a color-modifying active ingredient; and (c) a cosmetically-acceptable carrier component.

2. The composition according to claim 1, wherein the color-modifying active ingredient comprises a component selected from the group consisting of dye precursors, direct dyes, and mixtures thereof.

3. The composition according to claim 1, wherein the color-modifying active ingredient comprises a dye precursor selected from the group consisting of developers, couplers, and mixtures thereof.

4. The composition according to claim 1, wherein the color-modifying active ingredient comprises a dye precursor selected from the group consisting of indole derivatives, indoline derivatives, and mixtures thereof.

5. The composition according to claim 1, wherein the color-modifying active ingredient comprises a direct dye, and wherein the composition is free of dye precursors.

6. The composition according to claim 1, wherein the color-modifying active ingredient comprises a cationic direct dye.

7. The composition according to claim 1, wherein the color-modifying active ingredient comprises a cationic direct dye and a dye precursor selected from the group consisting of indole derivatives, indoline derivatives, and mixtures thereof.

8. The composition according to claim 5, wherein the direct dye comprises a cationic direct dye.

9. The composition according to claim 1, wherein the color-modifying active ingredient comprises a peroxo compound.

10. The composition according to claim 1, wherein the color-modifying active ingredient comprises a peroxo compound, and wherein the composition is free of dye precursors.

11. The composition according to claim 1, wherein the color-modifying active ingredient comprises a peroxo compound and a dye precursor selected from the group consisting of indole derivatives, indoline derivatives, and mixtures thereof.

12. The composition according to claim 1, wherein the protein is obtained from a seed of a *Moringa oleifera* plant.

13. The composition according to claim 4, wherein the protein is obtained from a seed of a *Moringa oleifera* plant.

14. The composition according to claim 6, wherein the protein is obtained from a seed of a *Moringa oleifera* plant.

15. The composition according to claim 9, wherein the protein is obtained from a seed of a *Moringa oleifera* plant.

16. The composition according to claim 1, wherein the protein is present as an extract from a seed of a plant of the *Moringa* genus.

17. The composition according to claim 16, wherein the extract is derived from the seed with a water-glycerol mixture.

18. A method comprising:
    (a) providing a composition comprising: (i) a protein from a seed of a plant of the *Moringa* genus; (ii) a color-modifying active ingredient; and (iii) a cosmetically-acceptable carrier component;
    (b) contacting a keratin fiber with the composition; and
    (c) removing the composition from the keratin fiber.

19. The method according to claim 18, further comprising combining the composition with an oxidizing agent prior to removal of the composition from the keratin fiber.

20. A method comprising: (a) providing a keratin fiber color-modifying active ingredient; and mixing the active ingredient with a protein from a seed of a plant of the *Moringa* genus.

* * * * *